United States Patent
Asgary

(10) Patent No.: US 8,105,086 B2
(45) Date of Patent: Jan. 31, 2012

(54) MEDICAL AND DENTAL BIOMATERIAL AND METHOD OF USE FOR THE SAME

(76) Inventor: Saeed Asgary, Tehran (IR)

(*) Notice: Subject to any disclaimer, the term of this patent is extended or adjusted under 35 U.S.C. 154(b) by 0 days.

(21) Appl. No.: 13/078,238

(22) Filed: Apr. 1, 2011

(65) Prior Publication Data

US 2011/0182995 A1 Jul. 28, 2011

Related U.S. Application Data

(63) Continuation of application No. 11/778,118, filed on Jul. 16, 2007, now Pat. No. 7,942,961.

(51) Int. Cl.
*A61C 5/02* (2006.01)
*A61C 5/04* (2006.01)

(52) U.S. Cl. .............. 433/224; 433/226; 433/228.1; 106/35; 106/691; 106/717

(58) Field of Classification Search .............. 433/215, 433/222.1, 224, 226
See application file for complete search history.

(56) References Cited

U.S. PATENT DOCUMENTS

| | | | | |
|---|---|---|---|---|
| 5,088,927 A * | 2/1992 | Lee | | 433/224 |
| 6,413,498 B1 * | 7/2002 | Malmagro | | 424/49 |
| 6,793,725 B2 * | 9/2004 | Chow et al. | | 106/35 |
| 7,838,573 B2 * | 11/2010 | Primus et al. | | 523/116 |
| 2002/0137812 A1 * | 9/2002 | Chow et al. | | 523/115 |
| 2005/0079470 A1 * | 4/2005 | Rutherford et al. | | 433/226 |
| 2006/0213395 A1 * | 9/2006 | Lu et al. | | 106/35 |
| 2007/0009858 A1 * | 1/2007 | Hatton et al. | | 433/224 |
| 2008/0318190 A1 * | 12/2008 | Suh et al. | | 433/228.1 |
| 2009/0148486 A1 * | 6/2009 | Lu et al. | | 424/422 |

* cited by examiner

*Primary Examiner* — Cris L Rodriguez
*Assistant Examiner* — Matthew Saunders
(74) *Attorney, Agent, or Firm* — Barry Choobin; Choobin & Choobin Consultancy

(57) ABSTRACT

The embodiments herein provide a dental and medical biomaterial and its use for sealing and/or filling the tooth and bone cavities. In the embodiments herein, the calcium salt, calcium oxide, calcium silicate, and calcium phosphate compounds are mixed with a water-base solution, and a bioactive phosphate and calcium enriched mixture is prepared. The mixture comprises high concentration of water-soluble calcium and phosphate, and consequently forms hydroxyapatite during and after setting. The dental/medical biomaterial is biocompatible, antibacterial and capable of forming an effective seal against reentrance of microorganisms into the filled cavity. The biomaterial is compatible to handle and set in an aqueous environment and to stimulate soft/hard tissue healing/generation/regeneration.

20 Claims, 15 Drawing Sheets

MEDICAL AND DENTAL BIOMATERIAL AND METHOD OF USE FOR THE SAME

CROSS-REFERENCE TO RELATED APPLICATIONS

This application is a continuation of application Ser. No. 11/778,118 filed Jul. 16, 2007 now U.S. Pat. No. 7,942,961.

The present invention is Sponsord by Iranian National Science Foundation.

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC

Not Applicable

BACKGROUND

1. Technical Field

The embodiments herein are generally related to a biomaterial predominantly medical or dental composition comprising bio-mineral materials. The embodiments herein particularly relate to a medical biomaterial that is suitable for bone filling during medical and dental surgeries. The embodiments herein more particularly relate to a dental specifically, endodontic biomaterial that is suitable for filling and sealing a tooth cavity or root canal during a dental or endodontic procedure in an orthograde or retrograde manner. The embodiments herein also relate to a composition having an enhanced adaptation to hydrophilic soft and hard tissues found within oral cavity that assist their ability to effectively fill and seal a newly shaped and cleaned tooth cavity or root canal system that subsequently forms hydroxyapatite to promote their sealing ability, biocompatibility, antibacterial effect and also stimulate the repair, regeneration and hard tissue formation.

2. Description of the Related Art

Endodontic treatment or root canal therapy (RCT) is a part of dentistry sciences that is generally indicated for teeth having sound external structures but diseased, dead or dying dental pulp and related tissues. Such teeth may or may not generally possess intact enamel or dentin and are satisfactorily engaged with surrounding bone tissue. A common aspect of endodontic treatment procedure involves a treatment of microorganism infected root canal systems. The procedure involves the following steps: a clinician's access to the root canal; removal of all the contents comprising potentially infected and diseased tissues, microorganisms and their by-products; disinfection of the root canal system using chemomechanical techniques; and application of special root canal instruments and irrigation devices to enlarge the root canal space and removal of irregularities or rough surfaces within the canal. It is important to fill and seal the root canal to preserve the dead tooth from further reentrance of microorganisms and recurrent decay that might compromise the integrity of the tooth and cause recontamination and infectious disease. Thus the pulp tissue and excised portions of the root are replaced by endodontic root canal filling materials that are materially safe, stable and biocompatible to living tissues, thereby keeping the tooth root safe to periradicular tissues.

The most common root canal filling material is made from "Gutta-Percha" which is a natural resin. A basic method involves inserting a pre-formed filling "cone" or "point" of gutta-percha into a root canal. The cone is then laterally or vertically condensed into the canal such that the point of the cone terminates at the apex of the canal. But, the remaining irregularities on the surface and in the shape of canal even after root canal shaping, and the non-adhesive character of gutta-percha had made it impossible to achieve a satisfactory, complete and tri-dimensional seal of the root canal system, from which any leakage of fluid containing microorganisms may occur in the case of using this material alone.

The filling and sealing of the root canal can be further enhanced by inserting sealants, flow-able and lubricant materials, along with the gutta-percha points. An ideal sealant should be biocompatible, anti-inflammatory, antibacterial, non-irritating, non-toxic, radiopaque and have no or minimal shrinkage or even have a slight expansion. It must be preferably unaffected by moisture and to the chemical and physical conditions of the mouth. Ideal prepared sealant has high wetting and low viscosity to facilitate insertion of filling material into the root canal so that the space between filling material and root canal walls is sealed.

Numerous sealants have been described, such as epoxy, calcium hydroxide and zinc oxide eugenol (ZOE) based sealers. During the RCT, the sealants are first applied to the gutta-percha and then inserted into the root canal along with each gutta-percha point or cone. Alternatively, they may be inserted using a file, reamer or lentulo applicator. In this way, it is hoped that the remaining spaces between the gutta-percha points and the root canal walls can be filled and sealed with the appropriate sealant material.

Controlling the exact amount of the sealant and filling material within the root canal to avoid overextension or overfilling has been a challenge for dentists. In the case of overflow of root canal sealant from the apical foramen into the periradicular tissue during a root canal filling process, the excess material should be desirably tolerated by the surrounding tissue while it is better for it to stimulate tissue healing.

One of the drawbacks of using conventional sealants is that such materials tend not to be hydrophobic. This makes such materials incompatible with somewhat moist dental hard/soft tissues within the root canal, which is therefore extremely hydrophilic. Thus the hydrophilic nature of the root canal environment inhibits adequate penetrance, complete wetting and efficient adhesion of the hydrophobic sealant to root canal walls. As a result, a poor seal is actually observed between the gutta-percha cones and the root canal walls, therefore it leads to reentrance of mouth microorganisms into the canal and helps them to multiply, which subsequently can be finalized as reinfection or other unwanted complications. Another point is that the overfilled materials tend not to have tolerance but also irritate the periapical soft tissues and do not stimulate healing and hard tissue formation.

While there are many techniques for root canal filling, as mentioned, the most widely used technique is the combination of gutta-percha cones and a sealant material. This technique has also been used with root-end fillings (also referred to as retrograde root canal fillings) during periradicular surgery and for the repair of tooth root perforations.

The function of an ideal root-end filling material is preparing perfect sealing ability in order to interfere with the path of reinfection of microorganism/byproducts completely, interrupting all paths between root canal system and its external surface. In addition, the root-end filling material should be antibacterial, nontoxic, noncorrosive, non-resorbable, dimensionally stable, easy handling, moisture indifferent, radiopaque, cost-effective, adaptable to the dentinal walls, and finally biocompatible and able to induce regeneration of the bone and periodontal attachment, specifically cementogenesis over the root-end filling itself.

The root-end filling materials were used to be the gutta-percha, amalgam, reinforced zinc oxide eugenol cement such as intermediate restorative material (IRM) and super EBA (Ethoxy Benzoic Acid), glass ionomer cement, and mineral trioxide aggregate (MTA) cement. The gutta-percha operation was so difficult, although amalgam has been used for more than a century and has proven itself well tolerated by oral tissues; unfortunately its use is disadvantageous for several reasons: it stains soft/hard tissues, eventually leaks from corrosion, is dimensionally unstable, and moisture sensitive. Reinforced zinc oxide eugenol cements have demerit of releasing eugenol and high-solubility, the IRM's weak point is its sensitivity to water, and the super EBA contained mass eugenol and the release of eugenol has high-solubility and inflammatory effect. The glass ionomer cement has sensitivity to water/moisture. The material property is thick. It is hard to dense-filling and difficult in handling. Although MTA has superior biocompatibility in comparison with the conventional root-end filling materials, it has delayed setting time, poor handling characteristics, and also a high price. Therefore a need for root-end filling materials remains that have good handling properties, and are capable of stimulating cementogenesis.

Management of non-vital open apex teeth is a great challenge in dentistry. The open apex is difficult to seal with conventional RCT. Multiple visit apexification with calcium hydroxide was the treatment of choice in children in order to induce apical hard tissue barrier. The long term use of calcium hydroxide has several disadvantages such as a need of high patient cooperation because the treatment takes a long period of time. Pulp revitalization is a regenerative approach that allows continuation of root development. The procedure is based on the concept that pulpal stem cells located in apical dental papilla and blood clot can survive pulpal necrosis. In this procedure after canal preparation, bleeding should be inducted into the canal. After that, the orifice of the canal should be filled/sealed with a biomaterial, therefore, a new pulpal tissue regenerates. There is a need for a suitable biomaterial for pulp revitalization in the art.

In case of root perforations, the filling material should be able to fill the perforation site effectively and seal the avenue of communication between the oral cavity and the underlying periodontium apparatus. For example, in a multi root tooth, the fork at the junction of the roots forms a "bi- or trifurcation." Thus, furcal perforations provide ready access of oral bacteria to the tissues of the gum. In the case of root perforation the clinician can also apply root-end fillings as mentioned before, so there is a need for a suitable perforation repair material in the art.

In contrast to RCT, in other certain dental procedures the pulp of the tooth is left intact. Where the pulp is exposed or partially damaged, a "pulp capping" or "pulpotomy" material is required which will preserve the vitality of the pulp. The material should also be biocompatible, bioactive, nontoxic, and without any irritation to the pulp. An ideal pulp capping or pulpotomy compound also allow the regeneration of surrounding tissue and dentine. Calcium hydroxide-based pulp capping/pulpotomy agents are therefore common. The calcium hydroxide technique has a very limited working time before setting. The material is degraded by long-term exposure to tissue fluids that are commonly present in the mouth and also is not impervious to moisture. It is difficult to form a hermetic seal with the calcium hydroxide filling materials. Therefore a need for pulp capping/pulpotomy materials remains which are biocompatible, bioactive, nontoxic, and are capable to stimulate dentinogenesis or dentin-like tissue formation.

Osseous defects may be caused by pathological diseases with endodontic/non-endodontic origin. Such defects may require surgical intervention, such as filling the defect with a bone filler biomaterial. It is important that the filler should be biocompatible and does not cause any additional trauma at the surgical site. The biomaterial may be a porous structure and may actively induce an in growth of adjacent bone tissue. Many products have been developed in an attempt to treat this surgical need. An example is autologous bone particles recovered from the patient where a significant increase in patient morbidity is attendant in this technique as the surgeon must take bone from a non-involved site in the patient. Another product group involves the use of inorganic materials; calcium sulfate may be mixed with water to form cement. This inorganic cement is osteoconductive but inert and do not absorb. It consequently remains in place indefinitely as a foreign body. Therefore a need for bone filler biomaterials remains, which are osteoinductive as well as osteoconductive, and are capable to stimulate osteogenesis.

A critical factor in the long-term success of RCT involves eliminating the leakage around and through a pulp capping/pulpotomy agent, root canal sealant, root canal filling, root-end filling, or the perforation repair material. Intimate adaptation of the filling material to the cavity walls typically plays an important role in elimination of the leakage. However, attaining intimate adaptation is difficult. Therefore, it is desirable to provide compositions and methods which improve the ability of penetrance, wetting, adaptation, filling, and sealing the dental soft and hard tissues surrounding the tooth cavity or root canal system for a dental material particularly in presence of moisture or water. Having antimicrobial effects and the ability to reduce or eliminate microorganisms, by-products, and their leakage would be an advantage for endodontic filling materials. Biocompatibility, of course, deserves to be mentioned as a high valuable point for these materials. It would be highly beneficial if the medical or dental biomaterial could be bioactive and stimulus for the repair and regeneration of the potentially surrounding blood, soft and hard tissues so that the pulp, dentin or dental-like hard tissues can be formed. It is also very desirable to provide compositions and methods which improve the osseous healing and osteogenesis after surgical intervention via osteoinduction or osteoconduction mechanisms.

Such compositions and methods for more effective filling and sealing of a tooth cavity, root canal system, or bone defect to induction of dentinogenesis, cementogenesis, and osteogenesis are disclosed and claimed herein.

The above mentioned shortcomings, disadvantages and problems are addressed herein and which will be understood by reading and studying the following specification.

OBJECTIVES OF THE EMBODIMENTS

The primary object of the embodiments herein is to provide a novel biomaterial that is compatible with the hydrophilic environment of mouth and provides an acceptable setting in the presence of moisture or blood.

Another object of the embodiments herein is to provide a novel dental or medical biomaterial and means for formulating the cement in such a way that the cement is easily prepared, transformed, placed, filled and the tooth cavity or bone cavity is completely sealed.

Yet another object of the embodiments herein is to provide a novel dental or medical biomaterial that does not show any shrinkage during its setting rather shows an expansion when used in a moist or wet field.

Yet another object of the embodiments herein is to provide a biomaterial that has a good adaptation with tooth cavity walls, hardens within a desired time and has resistance against being washed out.

Yet another object of the embodiments herein is to provide a biomaterial that is easy to remove while in the presence of excess biomaterial during tooth filling process.

Yet another object of the embodiments herein is to provide a medical and dental biomaterial that has a good adaptation to dentinal walls and improved sealing ability.

Yet another object of the embodiments herein is to provide a medical and dental biomaterial that contains antimicrobial agents such as calcium hydroxide and calcium oxide that reduce the existence of microorganisms and neutralize their by-products.

Yet another object of the embodiments herein is to provide a medical and dental biomaterial that gives an extra antimicrobial effect in sealing areas and reduces the possibility of infection or further decay of the tooth structure.

Yet another object of the embodiments herein is to provide a medical and dental biomaterial that can be easily sterilized.

Yet another object of the embodiments herein is to provide a medical and dental biomaterial that is bioactive and biocompatible and favorably allows dental and bone tissues healing and regeneration.

Yet another object of the embodiments herein is to provide a medical and dental biomaterial in which the bioactive particles in the cement composition are characterized by their ability to form hydroxyapatite i.e. the principal mineral in teeth and bones, and also stimulation and promotion of tissue repair and regeneration in contact to living dental and bone tissues.

Yet another object of the embodiments herein is to provide a medical and dental biomaterial that hardens at body temperature and reacts well in contact with tissue fluids.

These and other objects and advantages of the embodiments herein will become readily apparent from the following detailed description taken in conjunction with the accompanying drawings.

SUMMARY OF THE EMBODIMENTS

The embodiments herein provide a process for hard tissue generation and regeneration using a medical or dental biomaterial. The embodiments herein disclose a medical or dental biomaterial and method of use for the same.

According to an embodiment herein, a method for hard tissue generation/regeneration using a medical and dental biomaterial comprises identifying an appropriate dental or a non-dental tissue as a site for an insertion of said biomaterial. An insertion site for said biomaterial is prepared in said identified dental or non-dental tissues. A powder component is prepared by mixing a plurality of calcium-compound powders. The plurality of calcium-compound powders is selected from a group comprising of calcium salt compound powder, calcium oxide compound powder, calcium silicate compound powder, and calcium phosphate compound powder.

A liquid component is prepared wherein said liquid component is selected from a group comprising of distilled water, deionized water, normal saline, phosphate buffer saline (PBS) solution, simulated body fluid (SBF) solution, blood and blood derivatives, water-base salt solutions. A pH of said water base salt solutions is alkaline or neutral or acidic pH.

A phosphate and calcium enriched cement mixture is prepared wherein said cement mixture is prepared by mixing said prepared powder component with said prepared liquid component. A ratio of said prepared liquid component to said prepared powder component is within a range of 20 to 60 weight percent.

The cement mixture is applied in a body adjacent tissue for inducing and substituting a dental or non-dental hard tissue to induce a generation and regeneration of said hard tissue. The cement mixture is applied fresh or the cement mixture is applied in a set. The cement mixture is applied in a treated form. The cement mixture is applied alone. The cement mixture is applied along with at least an active additive. The cement mixture is applied along with at least a non-active additive.

The generation and regeneration of hard tissue includes a process selected from a group comprising of an osteogenesis, a dentinogenesis, a cementogenesis, and a pulp revitalization processes at said site.

The calcium salt compound powder is selected from a group comprising of calcium sulfate, calcium carbonate, calcium aluminate, calcium lactate, calcium nitrate, calcium citrate, calcium acetate, calcium stearate, calcium fumarate, calcium malate, calcium chloride, calcium bromide, calcium fluoride, calcium iodide, calcium saccharate, calcium oxalate, calcium gluconate, calcium propionate, calcium caseinate, calcium glycerophosphate, and combinations thereof.

The calcium oxide compound powder is selected from a group comprising of calcium oxide, calcium peroxide, calcium hydroxide, and combinations thereof.

The calcium silicate compound powder is selected from a group comprising of tetracalcium silicate, tricalcium silicate, dicalcium silicate, monocalcium silicate, amorphous calcium silicate and combinations thereof. The calcium phosphate compound powder is selected from a group comprising of octacalcium phosphate, heptacalcium phosphate, pentacalcium phosphate, tetracalcium phosphate, tricalcium phosphate, dicalcium phosphate, monocalcium phosphate, calcium pyrophosphate, calcium metaphosphate, calcium phosphinate, amorphous calcium phosphate, calcium hydroxide phosphate and combinations thereof.

The at least an active additive and at least a non-active additive is selected from a group comprising of therapeutic materials, bioactive molecules, biomaterials, biominerals, hydroxyapatite, bioactive calcium phosphate, gutta-percha, latex, antibiotics, medicaments, antibacterial agents, anti-viral agents, cariostatics, gelling agents, anti-inflammatory agents, anti-oxidants, adhesives, crystal adjustors, viscosity modifiers, preservatives, plasticizers, pore forming agents, fibers and meshes, metals, oxides, bone chips, bone crystals, organic and mineral fraction of bones and teeth, polymeric resins, resorbable and biodegradable and nonresorbable and naturally-occurring and synthetic polymers and copolymers, biologic factors, bioactive substances and cells, drugs, proteins, hormones, enzymes, antigens, immunogens, cytotoxins, neurotransmitters, interferons, interleukins, chemokines, cytokines, extracellular matrix components, synthetic peptide containing powder, adhesion molecules, ligands and peptides, osteoinductive factors, nano-particles, nanotubes, nanofibers, and combinations thereof.

The powder component and said liquid component are further added with one or more active additives or one or more non-active additives. The one or more active additives and one or more non-active additives are selected from a group comprising of filler materials, radiopaque materials, therapeutic materials, bioactive molecules, biomaterials, minerals, biominerals, bioceramics, bioglass, bioactive and biocompatible glass ceramics, apatite, hydroxyapatite, oxyapatite, apatite fluoride, fluorine-hydroxylapatite, carbonated hydroxyapatite, bioactive calcium phosphate, Portland cement, calcium-silicate and calcium-aluminate cement, silica, fumed silica, amorphous silica, silicate glass, alpha-whitlockite, beta-whitlockite, lithium silicate, glass fiber, quartz, fluoride preparation, gutta-percha, latex, antibiotics, medicaments, antibacterial agents, anti-viral agents, cariostatics, gelling agents, anti-inflammatory agents, anti-oxidants, alkaline earth metal silicate crystals, pigments/dyes, adhesives, crystal adjustors, viscosity modifiers, preservatives, plasticizers, pore forming agents, fibers/meshes, metals, zinc oxide, zirconia, alumina, zirconia-alumina ceramic, bismuth subcarbonate, tin oxide, titania, bone chips, bone crystals, organic and mineral fraction of bones and teeth, polymeric resins, resorbable and biodegradable and nonresorbable and naturally-occurring and synthetic polymers and copolymers, biologic factors, bioactive substances, drugs, proteins, hormones, enzymes, antigens, immunogens, cytotoxins, neurotransmitters, interferons, interleukins, chemokines, cytokines, extracellular matrix components, synthetic peptide containing powder, adhesion molecules, ligands and peptides, osteoinductive factors, nano-particles, nanotubes, nanofibers, and combinations thereof.

A concentration of said calcium salt compound powder, calcium oxide compound powder, calcium silicate compound powder, calcium phosphate compound powder, and an active additive or non-active additive in the biomaterial is within 0.5 to 98 percent by weight. A ratio of said liquid component to said powder component is within a range of 20 to 100 weight percent.

The powder component is prepared in a particulate form and wherein said powder component is prepared in a fibrous form and wherein a size of the powdered component is selected from a group comprising of a nanosized particle, a microsized particle, a macrosize particle, and mixtures thereof.

The powder component and said liquid component are mixed to produce a mixture. The mixture is treated in single phase alone. The mixture is treated in multi phases alone. The mixture is treated in single phase with a third component. The mixture is treated in multi phases with a third component. The third component comprises of at least one said active additive material. The third component comprises a non-active additive material.

The mixture is treated to produce a treated set cement in a form. The form is selected from a group comprising of a three-dimensional scaffold and shaped pieces, particulates, a fine and coarse free encapsulated powders, a pellets, microspheres, macrospheres, a porous structure, a macroporous structure, a microporous structures, a compact material, a thin layer, a thin film, granulated form, an implantable device, a coating, a paste and a prefabricated kit in association with and without said cells. The three-dimensional scaffolds and shaped pieces is osteoconductive and osteoinductive.

The mixture is ground to produce a micro particle and a macro-particles. The micro particles and the macro-particles contact with a solution to obtain a precipitate of calcium and phosphate on a surface of the micro particles and the macro-particles. The precipitate of calcium and phosphate is hydroxyapatite crystal. The micro particles and the macro-particles are removed from the solution. The solution is selected from a group comprising of an aqueous salt solution, a blood and a blood derivative containing calcium and phosphate ions. The aqueous salt solution and the blood and the blood derivative containing calcium and phosphate ions act as a biomaterial covered with calcium-phosphate.

The resorbable and biodegradable or nonresorbable and naturally occurring or synthetic polymer or copolymer material is selected from a group comprising of hydroxy acids, polyamides, polyesters, polyurethanes, poly(vinyl alcohol), poly(ethylene glycol), pluronic, poly(vinylpyrrolidone), cellulose, cellulose acetate, hydroxyethyl cellulose, hydroxypropyl cellulose, carboxymethyl cellulose, poly(ethylene terephthalate), poly(anhydride), poly(propylene fumarate), collagen, fibrin, matrigel, alginate, modified alginate, elastin, chitosan, chitin, gelatin, polylactic acid (PLA) polymer, polyglycolic acid (PGA) polymer, polylactic-co-glycolic acid (PLG/PLGA), poly(D,L-lactic acid) (PDLLA), Poly(ε-caprolactone) (PCL), polycarbonates, polyesteramides (PEA), poly-p-dioxanone (PDS), poly-beta-hydroxypropionic acid (PHPA), poly-beta-hydroxyvaleric acid (PHVA), glycolide/trimethylenecarbonate copolymer (PGA/TMC), poly-beta-hydroxybutyric acid (PHBA), glycolide/lactide copolymer (PGA/PLA) copolymer, poly(acrylonitrile-co-vinyl chloride), and polylysine, polysulfone, and combinations thereof.

The process of preparing a powder comprising calcium-silicate and calcium-aluminate cement comprises homogenizing a calcium carbonate, a silica, and an alumina to produce a mixture using a wet technique. A ratio of the calcium carbonate ($CaCO_3$) in the mixture is within 60-80% by weight. A ratio of the silica ($SiO_2$) in the mixture is within 20-35% by weight. A ratio of the alumina ($Al_2O_3$) in the mixture is within 1-10%. The mixture is dried at a temperature above 100° C. for 24 h. The dried mixture is ground to produce a powder. The powder in a wet form is shaped and compacted to produce a bulk. The bulk is melted at a temperature ranging up to 1650° C. to produce a melt solution. The melt solution is quenched. The quenched melt is grinded to produce a powder. An amount of the calcium-silicate and calcium-aluminate cement present in the prepared powder in the biomaterial is up to 98 weight percent.

The radiopaque material is selected from a group comprising of a salt, an oxide of silver, barium, strontium, titanium, bismuth; a metal; heavy metals containing glass frits; a compound containing tungsten; an organo-iodine compound, and a combination thereof and wherein an amount of said radiopaque material is up to 48 weight percent.

The nano-particle comprises at least one nano-particle selected from a group consisting of nano-silica, nano-titanium oxide, nano-iron, nano-iron oxide, nano-alumina, nano-zinc oxide, nano-boron, nano-calcium carbonate, nano-clay; nanotubes; nanofibers; nanocomposites, and combinations thereof and wherein an amount of said nano-particle is within 0.5 to 25 percent by weight.

The process of inducing a hard tissue in dental tissue comprises identifying a tooth cavity to be filled and the tooth cavity comprises of a cavity selected from a group comprising of a cavity with Class I to Class VI standard, a non-standard tooth cavity, a pulp chamber with partial pulpotomy, a pulp chamber with complete pulpotomy, a root canal, a root perforation, a root resorption, an internal root resorption an external root resorption, and a root-end cavity. The cavity to be filled is prepared in a tooth. Then the biomaterial is prepared and applied into the tooth cavity.

A first seal is creating for the tooth cavity. The first seal is increased by expanding the biomaterial three dimensionally. The biomaterial is expanded along a length direction, a width direction and a height direction. A biological active material is released from the biomaterial for promoting a tissue generation and a tissue regeneration in the tooth cavity to create an antibacterial environment in the tooth cavity as well as to create a second seal over the first seal via hydroxyapatite formation. The process of promoting tissue generation/regeneration includes a pulp revitalization, a dentinogenesis, and a cementogenesis.

The process for inducing or substituting a hard tissue in bone comprises identifying a site to be restored in a bone and preparing the site to be restored in the bone. The biomaterial is prepared and applied into the insertion site of the bone. A biological active material is released from the biomaterial for osteoinduction or osteoconduction to promote osteogenesis thereby progressively replacing said biomaterial with a natural bone.

The method further comprises modifying a plurality of components present in the powder component and a mixing ratio of said plurality of components in the powder component and in the liquid component to develop a plurality of fast setting or non-fast setting biomaterials in a dental or a medical kit. The dental or medical kit is used for treating an application. The application is selected from a group comprising of vital pulp therapy, direct/indirect pulp capping, pulpotomy, pulp revitalization, root canal sealant, root canal filling, perforation repair, root-end filling, implant material, bone cement, bone filler, and other clinical applications.

The method comprising: identifying an appropriate dental and non-dental tissue as the site for insertion of the biomaterial; preparing the insertion site for the biomaterial in the identified dental and non-dental tissues; preparing a powder component by mixing a plurality of calcium-compound powders and at least an active or non-active additive material; wherein said plurality of calcium-compound powders consist of calcium salt compound powder, calcium oxide compound powder, calcium silicate compound powder, and calcium phosphate compound powder; preparing a liquid component, wherein said liquid is either distilled water, deionized water, or water-base salt solutions with alkaline, neutralized or acidic pH; preparing a phosphate and calcium enriched mixture cement, wherein said mixture is prepared by mixing said powder component with said liquid component, wherein a ratio of said liquid to said powder is in a range of 20 to 50 weight percent; and applying fresh, set or treated form of said mixture either alone, or via encapsulation or assembling or coating onto an implantable device or scaffold, in the body adjacent tissue for dental and/or non-dental hard tissue induction or substitution; thereby inducing hard tissue generation or regeneration i.e. osteogenesis, dentinogenesis, cementogenesis, and pulp revitalization at the site. Such material and method satisfy the existing needs i.e. control of infection, osteoinduction, etc. by providing an antibacterial effect, biocompatibility, stimulation of repair and regeneration i.e. pulp revitalization, hard tissue formation i.e. dentinogenesis, cementogenesis, osteogenesis, and improving the seal against invasive microorganisms and/or their by-products in an aqueous environment.

The embodiments herein provide a method for preparing a novel medical or dental biomaterial and its usage. The method for hard tissue generation/regeneration using a medical/dental biomaterial comprising: identifying an appropriate dental/non-dental tissue as the site for insertion of the biomaterial; preparing the insertion site for the biomaterial in the identified dental/non-dental tissues; preparing a powder component by mixing a plurality of calcium-compound powders; wherein the plurality of calcium-compound powders is selected from a group comprising of calcium salt compound powder, calcium oxide compound powder, calcium silicate compound powder, and calcium phosphate compound powder; preparing a liquid component, wherein the liquid is either distilled/deionized water, or water-base salt solutions with alkaline, neutral or acidic pH; preparing a phosphate and a calcium enriched mixture cement, wherein the mixture cement is prepared by mixing the powder component with the liquid component, wherein a ratio of the liquid component to the powder component is in a range of 20 to 60 weight percent; and applying a fresh, set or a treated form of the mixture cement either alone, or along with at least an active/non-active additive, in a body adjacent tissue for dental/non-dental hard tissue induction/substitution; thereby inducing the hard tissue generation/regeneration including osteogenesis, dentinogenesis, cementogenesis, and pulp revitalization at the site.

According to one embodiment herein, the calcium salt compound powder is selected from a group comprising of calcium sulfate, calcium carbonate, calcium aluminate, calcium lactate, calcium nitrate, calcium citrate, calcium acetate, calcium stearate, calcium fumarate, calcium malate, calcium chloride, calcium bromide, calcium fluoride, calcium iodide, calcium saccharate, calcium oxalate, calcium gluconate, calcium propionate, calcium caseinate, calcium glycerophosphate, and combinations thereof.

According to another embodiment herein, the calcium oxide compound powder is selected from a group comprising of calcium oxide, calcium peroxide, calcium hydroxide, and combinations thereof.

According to one embodiment herein, the calcium silicate compound powder is selected from a group comprising of tetracalcium silicate, tricalcium silicate, dicalcium silicate, monocalcium silicate, amorphous calcium silicate and combinations thereof.

According to another embodiment herein, the calcium phosphate compound powder is selected from a group comprising of octacalcium phosphate, heptacalcium phosphate, pentacalcium phosphate, tetracalcium phosphate, tricalcium phosphate, dicalcium phosphate, monocalcium phosphate, calcium pyrophosphate, calcium metaphosphate, calcium phosphinate, amorphous calcium phosphate, calcium hydroxide phosphate and combinations thereof.

According to one embodiment herein, the active/non-active additive is selected from a group comprising of therapeutic materials, bioactive molecules, biomaterials, biominerals, hydroxyapatite, bioactive calcium phosphate, gutta-percha, latex, antibiotics, medicaments, antibacterial agents, anti-viral agents, cariostatics, gelling agents, anti-inflammatory agents, anti-oxidants, adhesives, crystal adjustors, viscosity modifiers, preservatives, plasticizers, pore forming agents, fibers/meshes, metals, oxides, bone chips, bone crystals, organic or mineral fraction of bones or teeth, polymeric resins, resorbable (biodegradable)/nonresorbable naturally-occurring/synthetic polymers/copolymers, biologic factors, bioactive substances/cells, drugs, proteins, hormones, enzymes, antigens, immunogens, cytotoxins, neurotransmitters, interferons, interleukins, chemokines, cytokines, extracellular matrix components, synthetic peptide containing powder, adhesion molecules, ligands or peptides, osteoinductive factors, nano-particles, nanotubes, nanofibers, and combinations thereof.

According to another embodiment herein, the powder component and the liquid component further adds one or more active/non-active additives, wherein the active/non-active additives are selected from a group comprising of filler materials, radiopaque materials, therapeutic materials, bioactive molecules, biomaterials, minerals/biominerals, bioceramics, bioglass, bioactive/biocompatible glass ceramics, apatite, hydroxyapatite, oxyapatite, apatite fluoride, fluorine-hydroxylapatite, carbonated hydroxyapatite, bioactive calcium phosphate, Portland cement, calcium-silicate/calcium-aluminate cement, silica, fumed silica, amorphous silica, silicate glass, alpha-whitlockite, beta-whitlockite, lithium silicate, glass fiber, quartz, fluoride preparation, gutta-percha, latex, antibiotics, medicaments, antibacterial agents, anti-viral agents, cariostatics, gelling agents, anti-inflammatory agents, anti-oxidants, alkaline earth metal silicate crystals, pigments/dyes, adhesives, crystal adjustors, viscosity modifiers, preservatives, plasticizers, pore forming agents, fibers/meshes, metals, zinc oxide, zirconia, alumina, zirconia-alumina ceramic, bismuth subcarbonate, tin oxide, titania, bone chips, bone crystals, organic or mineral fraction of bones or teeth, polymeric resins, resorbable (biodegradable)/nonresorbable naturally-occurring/synthetic polymers/copolymers, biologic factors, bioactive substances, drugs, proteins, hormones, enzymes, antigens, immunogens, cytotoxins, neurotransmitters, interferons, interleukins, chemokines, cytokines, extracellular matrix components, synthetic peptide containing powder, adhesion molecules, ligands or peptides, osteoinductive factors, nano-particles, nanotubes, nanofibers, and combinations thereof.

The concentration of the calcium salt compound powder, calcium oxide compound powder, calcium silicate compound powder, calcium phosphate compound powder, and active/non-active additive in the biomaterial is within 0.5 to 98 percent by weight.

According to one embodiment herein, the liquid component includes a water base solution selected from a group comprising of deionized water, distilled water, normal saline, phosphate buffer saline (PBS) solution, simulated body fluid (SBF) solution, blood and blood derivatives, and salt solution with alkaline, neutral or acidic pH and wherein a ratio of the liquid component to the powder component is in a range of 20 to 100 weight percent.

According to another embodiment herein, the powder component is in the form of a particulate or fibrous and in a nanosize, microsize, macrosize, or mixtures thereof, and wherein the powder component and the liquid component are mixed to produce a mixture, wherein the mixture is treated in single or multi phases alone or with a third component, wherein the third component comprises of at least one the active/non-active additive, wherein the treated mixture produces a treated set cement in a form, wherein the forms includes a three-dimensional scaffold/shaped pieces, particulates, fine or coarse free/encapsulated powders, pellets, microspheres, macrospheres, porous, macroporous and microporous structures, compact material, a thin layer/films, granulated form, implantable device, coatings, paste or a prefabricated kit in association with/without the cells. The three-dimensional scaffolds or shaped pieces is osteoconductive and osteoinductive.

The set mixture grinds to produce a micro/macro-particles, wherein the particles contact with an aqueous salt solution or a blood and a blood derivatives containing calcium and phosphate ions thereby consequently precipitate a calcium-phosphate i.e. hydroxyapatite crystal on the surface of the particles, and removing the composite particles from the aqueous salt solution or the blood and the blood derivatives as a calcium-phosphate-covered biomaterial.

The resorbable (biodegradable)/nonresorbable naturally occurring/synthetic polymer/copolymer material is selected from a group comprising of a hydroxy acids, polyamides, polyesters, polyurethanes, poly (vinyl alcohol), poly(ethylene glycol), pluronic, poly(vinylpyrollidone), cellulose, cellulose acetate, hydroxyethyl cellulose, hydroxypropyl cellulose, carboxymethyl cellulose, poly(ethylene terephthalate), poly(anhydride), poly (propylene fumarate), collagen, fibrin, matrigel, alginate, modified alginate, elastin, chitosan, chitin, gelatin, polylactic acid (PLA) polymer, polyglycolic acid (PGA) polymer, polylactic-co-glycolic acid (PLG/PLGA), poly(D,L-lactic acid) (PDLLA), Poly($\epsilon$-caprolactone) (PCL), polycarbonates, polyesteramides (PEA), poly-p-dioxanone (PDS), poly-beta-hydroxypropionic acid (PHPA), poly-beta-hydroxyvaleric acid (PHVA), glycolide/trimethylenecarbonate copolymer (PGA/TMC), poly-beta-hydroxybutyric acid (PHBA), glycolide/lactide copolymer (PGA/PLA) copolymer, poly(acrylonitrile-co-vinyl chloride), or polylysine, polysulfone, and combinations thereof.

According to one embodiment herein, the process for preparing calcium-silicate/calcium-aluminate cement, comprising the steps of: homogenizing calcium carbonate, silica, and alumina to produce a mixture having the following proportions: $CaCO_3$ 60-80%, $SiO_2$ 20-35%, and $Al_2O_3$ 1-10% by weight using wet technique; drying the mixture at >100° C. for 24 h; grinding the dried mixture to produce a powder; shaping and compacting the powder in wet form to produce a bulk; melting the bulk at a temperature ranging up to 1650° C. to produce a melt; quenching the melt; and grinding the quenched melt to produce a powder, wherein an amount of the calcium-silicate/calcium-aluminate cement in the biomaterial is up to 98 weight percent.

The radiopaque material is selected from a group comprising a salt or oxide of silver, barium, strontium, titanium, or bismuth; a metal; glass frits containing heavy metals; a tungsten-containing compound; an organo-iodine compound, or a combination thereof and wherein an amount of the radiopaque material is up to 48 weight percent.

The nano-particle comprises at least one nano-particle selected from a group consisting of nano-silica, nano-titanium oxide, nano-iron, nano-iron oxide, nano-alumina, nano-zinc oxide, nano-boron, nano-calcium carbonate, nano-clay; nanotubes; nanofibers; nanocomposites, and combinations thereof and wherein an amount of said nano-particle is within 0.5 to 25 percent by weight.

According to another embodiment herein, the method of hard tissue induction of dental tissues, comprising the steps of: identifying a tooth cavity, wherein the tooth cavity comprises a standard i.e. Class I to Class VI, a non-standard tooth cavity preparation, a pulp chamber (partial/complete pulpotomy), a root canal, a root perforation, a root resorption, an internal/external root resorption, and a root-end cavity, to be filled; preparing the cavity to be filled in a tooth; preparing the biomaterial; applying the biomaterial into the tooth cavity; creating a first seal for the tooth cavity; increasing the first seal by tri-dimensional expansion of the biomaterial; releasing biological active material from the biomaterial, thereby creating an antibacterial environment in the tooth cavity as well as creating a second seal over the first seal via hydroxyapatite formation, thereby promoting tissue generation/regeneration including pulp revitalization, dentinogenesis, and cementogenesis.

According to another embodiment herein, the method of hard tissue induction/substitution of bone, comprising the steps of: identifying a site to be restored in a bone; preparing the site to be restored in the bone; preparing the biomaterial; applying the biomaterial into the insertion site of the bone; releasing a biological active material from the biomaterial for osteoinduction/osteoconduction, thereby promoting osteogenesis and the biomaterial is progressively replaced with natural bone.

The modification of the powder/liquid components and/or ratios develops a several fast/non-fast setting biomaterials in a dental/medical kit for vital pulp therapy, direct/indirect pulp capping, pulpotomy, pulp revitalization, root canal sealant, root canal filling, perforation repair, root-end filling, implant material, bone cement, bone filler, and other clinical applications.

The cement components that is a novel medical or dental biomaterial provides a prefabricate kit that also contains the description for methods of its use.

These and other aspects of the embodiments herein will be better appreciated and understood when considered in conjunction with the following description and the accompanying drawings. It should be understood, however, that the following descriptions, while indicating preferred embodiments and numerous specific details thereof, are given by way of illustration and not of limitation. Many changes and modifications may be made within the scope of the embodiments herein without departing from the spirit thereof, and the embodiments herein include all such modifications.

BRIEF DESCRIPTION OF THE DRAWINGS

The other objects, features and advantages will occur to those skilled in the art from the following description of the preferred embodiment and the accompanying drawings in which.

Figure 1:
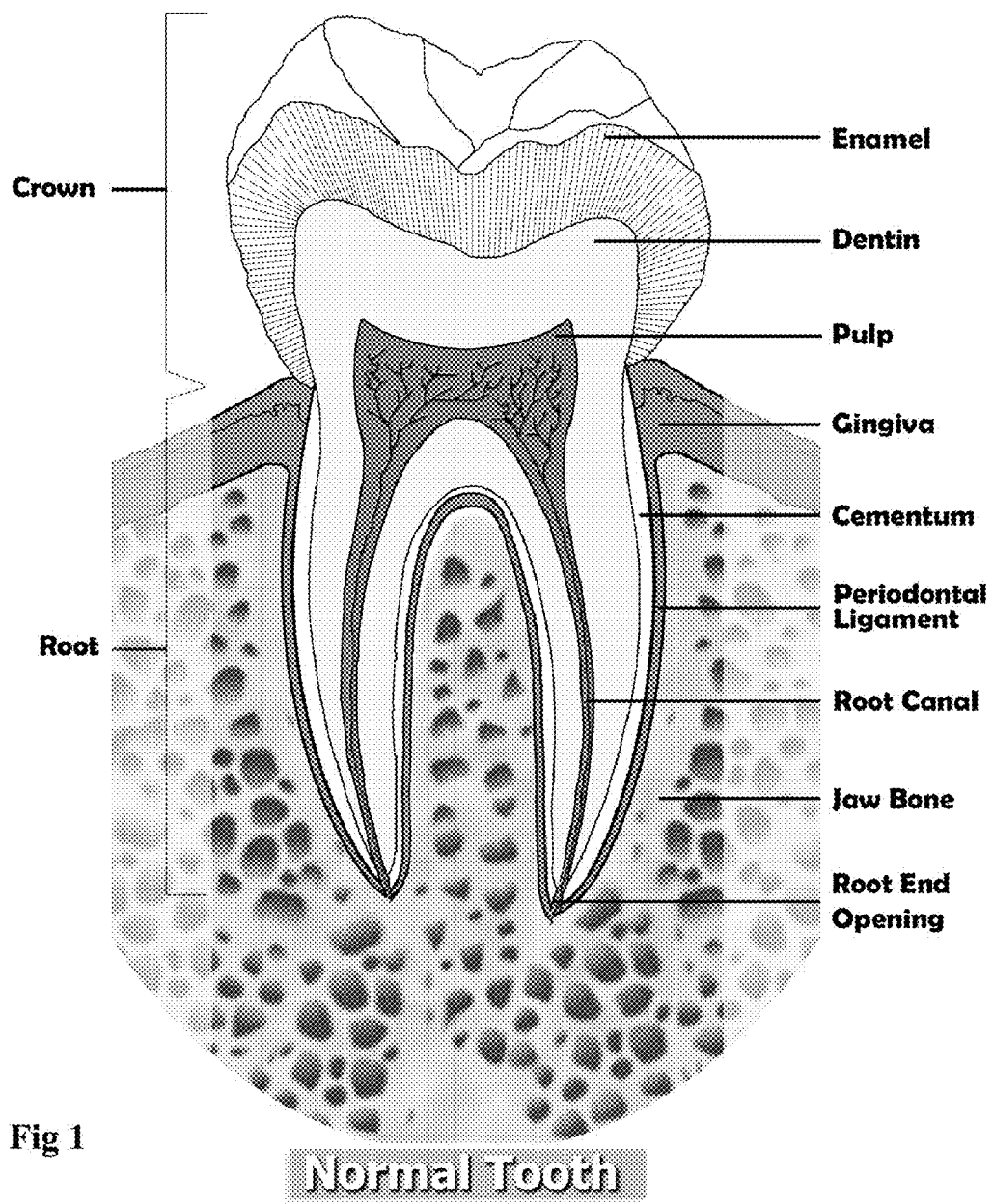
FIG. 1 is a longitudinal view of a healthy mandibular molar tooth showing two roots, a normal pulp and root canals.

These and other aspects of the embodiments herein will be better appreciated and understood when considered in conjunction with the following description and the accompanying drawings. It should be understood, however, that the following descriptions, while indicating preferred embodiments and numerous specific details thereof, are given by way of illustration and not of limitation. Many changes and modifications may be made within the scope of the embodiments herein without departing from the spirit thereof, and the embodiments herein include all such modifications.

DETAILED DESCRIPTION OF THE EMBODIMENTS

In the following detailed description, a reference is made to the accompanying drawings that form a part hereof, and in which the specific embodiments that may be practiced is shown by way of illustration. The embodiments are described in sufficient detail to enable those skilled in the art to practice the embodiments and it is to be understood that the logical, mechanical and other changes may be made without departing from the scope of the embodiments. The following detailed description is therefore not to be taken in a limiting sense.

The various embodiments herein provide a medical and dental biomaterial and a method of making the same. The medical or dental biomaterial that is a bioactive cement and method of use for filling tooth cavity, root canals and bone defect comprises: identifying an appropriate dental or non-dental tissue as the site for insertion of the biomaterial; preparing the insertion site for the biomaterial in the identified dental or non-dental tissues; preparing a powder component by mixing a plurality of calcium-compound powders; wherein the plurality of calcium-compound powders consist of calcium salt compound powder, calcium oxide compound powder, calcium silicate compound powder, and calcium phosphate compound powder; preparing a liquid component, wherein the liquid is either distilled or deionized water, or water-base salt solutions with alkaline, neutralized or acidic pH; preparing a phosphate and calcium enriched mixture cement, wherein the mixture cement is prepared by mixing the powder component with the liquid component, wherein a ratio of the liquid to the powder is in a range of 20 to 60 weight percent; and applying fresh, set, or treated form of the mixture cement either alone, or along with at least an active or non-active additive, in the body adjacent tissue for dental or non-dental hard tissue induction/substitution, thereby inducing hard tissue generation/regeneration including osteogenesis, dentinogenesis, cementogenesis, and pulp revitalization at the site. An active or non-active additive material is added to the mixture cement to achieve a better clinical outcome. The composition include at least an active or non-active additive selected from a group comprising of therapeutic materials, bioactive molecules, biomaterials, biominerals, hydroxyapatite, bioactive calcium phosphate, gutta-percha, latex, antibiotics, medicaments, antibacterial agents, anti-viral agents, cariostatics, gelling agents, anti-inflammatory agents, anti-oxidants, adhesives, crystal adjustors, viscosity modifiers, preservatives, plasticizers, pore forming agents, fibers/meshes, metals, oxides, bone chips, bone crystals, organic or mineral fraction of bones or teeth, polymeric resins, resorbable (biodegradable)/nonresorbable naturally-occurring/synthetic polymers/copolymers, biologic factors, bioactive substances/cells, drugs, proteins, hormones, enzymes, antigens, immunogens, cytotoxins, neurotransmitters, interferons, interleukins, chemokines, cytokines, extracellular matrix components, synthetic peptide containing powder, adhesion molecules, ligands or peptides, osteoinductive factors, nanoparticles, nanotubes, nanofibers, and combinations thereof.

Suitable calcium salt, calcium oxide, calcium silicate, and calcium phosphate compounds for use as the plurality of calcium-compounds in the powder component of mixture are biologically active and compatible. It is preferred that the plurality of calcium-compounds in powder is stimulatable by mixing with its solution and/or body tissue fluids and/or blood. Examples of appropriate calcium salt compounds including but are not limited to calcium sulfate, calcium carbonate, calcium aluminate, calcium lactate, calcium nitrate, calcium citrate, calcium acetate, calcium stearate, calcium fumarate, calcium malate, calcium chloride, calcium bromide, calcium fluoride, calcium iodide, calcium saccharate, calcium oxalate, calcium gluconate, calcium propionate, calcium caseinate, calcium glycerophosphate, and combinations thereof. Examples of appropriate calcium oxide compounds including but are not limited to calcium oxide, calcium peroxide, calcium hydroxide, and combinations thereof. Examples of appropriate calcium silicate compounds including but are not limited to tetracalcium silicate, tricalcium silicate, dicalcium silicate, monocalcium silicate, amorphous calcium silicate and combinations thereof. Examples of appropriate calcium phosphate compounds including but are not limited to octacalcium phosphate, heptacalcium phosphate, pentacalcium phosphate, tetracalcium phosphate, tricalcium phosphate, dicalcium phosphate, monocalcium phosphate, calcium pyrophosphate, calcium metaphosphate, calcium phosphinate, amorphous calcium phosphate, calcium hydroxide phosphate and combinations thereof, wherein a concentration of calcium salt compound powder, calcium oxide compound powder, calcium silicate compound powder, and calcium phosphate compound powder in the biomaterial is within 0.5 to 98 percent by weight.

Preferred calcium salt, calcium oxide, calcium silicate, and calcium phosphate compounds selected from the above list are the tricalcium silicate, dicalcium silicate, tricalcium phosphate, dicalcium phosphate, calcium oxide, calcium hydroxide, calcium sulfate, calcium carbonate, calcium chloride, calcium aluminate, and calcium fluoride. The biominerals are used to advantage the medical/dental biomaterial in part because of their excellent biocompatibility. In the presence of an aqueous environment, these biominerals produce a large amount of hydroxyl, calcium, and phosphate ions that readily alter and raise the pH of area, form hydroxyapatite ($Ca_5(PO_4)_3OH$) crystals, increase antibacterial activity, stimulate and promote hard tissue formation, and the body tolerates the excess amount. The preferred biominerals/materials are present in an amount up to 98 percent by weight.

A suitable active/non-active additive material as dentin, cementum, pulp or bone growth promoting substance including but are not limited to filler materials, radiopaque materials, therapeutic materials, bioactive molecules, biomaterials, minerals/biominerals, bioceramics, bioglass, bioactive/biocompatible glass ceramics, apatite, hydroxyapatite, oxyapatite, apatite fluoride, fluorine-hydroxylapatite, carbonated hydroxyapatite, bioactive calcium phosphate, Portland cement, calcium-silicate/calcium-aluminate cement, silica, fumed silica, amorphous silica, silicate glass, alpha-whitlockite, beta-whitlockite, lithium silicate, glass fiber, quartz, fluoride preparation, gutta-percha, latex, antibiotics, medicaments, antibacterial agents, anti-viral agents, cariostatics, gelling agents, anti-inflammatory agents, anti-oxidants, alkaline earth metal silicate crystals, pigments/dyes, adhesives, crystal adjustors, viscosity modifiers, preservatives, plasticizers, pore forming agents, fibers/meshes, metals, zinc oxide, zirconia, alumina, zirconia-alumina ceramic, bismuth subcarbonate, tin oxide, titania, bone chips, bone crystals, organic or mineral fraction of bones or teeth, polymeric resins, resorbable (biodegradable)/nonresorbable naturally-occurring/synthetic polymers/copolymers, biologic factors, bioactive substances, drugs, proteins, hormones, enzymes, antigens, immunogens, cytotoxins, neurotransmitters, interferons, interleukins, chemokines, cytokines, extracellular matrix components, synthetic peptide containing powder, adhesion molecules, ligands or peptides, osteoinductive factors, nano-particles, nanotubes, nanofibers, combinations thereof, and the like. The active/non-active additive material undergoes chemical reactions at the interface between the soft or hard tissues and the medical/dental biomaterial herein containing the bioactive material. The regeneration or repair of destroyed or damaged surrounding tissues will be allowed simultaneously. The active/non-active additive materials are used in an amount of up to about 96 percent by weight of the composition.

The medical/dental biomaterial includes at least an active/non-active additive material. Preferred active/non-active additive materials selected from a group comprising of filler materials, radiopaque materials, therapeutic materials, biomaterials, biominerals, hydroxyapatite, calcium-silicate/calcium-aluminate cement, silica, antibiotics, medicaments, antibacterial agents, anti-viral agents, anti-inflammatory agents, anti-oxidants, pigments/dyes, plasticizers, pore forming agents, fibers/meshes, zinc oxide, zirconia, alumina, zirconia-alumina ceramic, titania, bone chips, bone crystals, organic or mineral fraction of bones or teeth, polymeric resins, resorbable (biodegradable)/nonresorbable naturally-occurring/synthetic polymers/copolymers, biologic factors, bioactive substances/cells, drugs, proteins, hormones, enzymes, osteoinductive factors, nanoparticles, nanotubes, nanofibers, and combinations thereof, which is compatible with soft and hard tissues and capable of promoting the growth, regeneration, and survival of cells, tissues, and bone. These preferred active/non-active additive material are present in an amount up to 98 percent by weight.

The particles of calcium salt/oxide/silicate/phosphate compounds and active/non-active additive may be in the form of a particulate or fibrous in nanosize, microsize, macrosize, or mixtures thereof. The characteristics of the cement composition depend upon the size of the particles, for example, nano-particles of calcium compounds will promote and accelerate hydroxyapatite formation and cement hardening The term "radiopaque" refers to a material that allows the composition to be more easily seen using an X-ray. The radiopaque filler provides the ability to determine how well the medical/dental biomaterial has penetrated into and filled the tooth cavity, root canal(s) and a bone defect. The radio-pacifiers used in biomaterial compositions include but are not limited to salt or oxide of silver (e.g. silver iodide), barium (e.g. barium sulfate), strontium (e.g. strontium sulfate, or strontium chloride), titanium (e.g. titanium dioxide), or bismuth (e.g. bismuth carbonate, bismuth subcarbonate, or bismuth trioxide); a metal (e.g. tungsten, or tantalum); glass frits containing heavy metal (e.g. barium or bismuths); a tungsten-containing compound; an organo-iodine compound; or mixtures thereof. The radiopacifiers are incorporated in the range of up to 48 percent by weight.

According to one embodiment herein, the medical/dental biomaterial includes antibacterial agent(s) to assist in cleansing and sterilizing the tooth cavity or root canal and to prevent later reinfections. Examples of suitable antibacterial agents are alkaline earth metal oxides (e.g. calcium oxide/peroxide), and alkaline earth metal hydroxides (e.g. calcium hydroxide). A more preferred antibacterial agent is calcium hydroxide. Calcium hydroxide not only kills microorganisms but is also chemically compatible with dental tissues. The antibacterial agent is included in the composition in a range of up to 48 percent by weight of the composition.

In many endodontic treatments, the ultimate success of the RCT often depends on the adaptation of the filling material to the tooth walls, and the resultant seal between the material and the tooth structures. An ideal seal prevents the leakage and migration of bacteria into the cavity. The sufficiency of the seal is particularly important where the pulp chamber or root canal system is to be sealed. The embodiments herein are directed to a dental biomaterial used to fill and seal a cavity or root canal(s). To provide better compatibility with the hydrophilic environment within a tooth or bone, the biomaterial advantageously includes components that are compatible with hydrophilic tissues. Increased hydrophilic compatibility facilitates wetting of the dental tissues, enables penetration of the biomaterial within gaps and spaces associated with the root canal(s), and also promotes penetration into the dentinal tubules. Further, the biomaterial in contrast with others not only shows no shrinkage but also demonstrates a slight expansion after its placement in cavity or root canal(s) and setting processes; therefore provides much better adaptation of the biomaterial to the tooth walls. The biomaterial also forms hydroxyapatite during and after setting and hardening, and provides an additional seal at the interface of the biomaterial and cavity walls, and the superficial aspect of the filling area and both. Because of these characteristics, the biomaterial prevents or significantly reduces microleakage when it is produced and used according to the embodiments herein. The biomaterial enhances the long-term success rate of a wide variety of dental treatments that may require a filling and sealing biomaterial.

The surface infiltration of the bioactive ingredient of the dental biomaterial permits bio-stimulation of the cement before, during and after hardening process, to create unique water-based, calcium and phosphate-containing, bio-mineral based composition that facilitates repair and the generation or regeneration of damaged tissues at one interface osteogenesis, dentinogenesis, cementogenesis, and pulp revitalization, while stabilizing the other surfaces and the bulk of cement with respect to sealing properties. Thus, the biomaterial becomes a unique optimized one with respect to biocompatibility, bioactivity and sealing ability.

The calcium salt, calcium oxide, calcium silicate and calcium phosphate compounds include a powder consisting of particles that are hydrophilic and that set in the presence of different kinds of water base solutions and include, but are not limited to, deionized or distilled water, normal saline, phosphate buffer saline (PBS) solution, simulated body fluid (SBF) solution, blood and blood derivatives, and salt solution with alkaline, neutral or acidic pH. The fact that water is necessary for hardening reaction offers a significant advantage over many of other commonly used dental materials by allowing the cement to set in the wet environment. Generally, the solutions can be divided in numerous groups based on the mechanism by which the solutions accelerate the cement setting reactions and its final properties and products. Mixing the cement with distilled/deionized water is the beginning phase of the complex reactions that results a colloidal gel yields a product that self-sets at the ambient or body temperatures to some stable substances such as calcium silicate hydrate and hydroxyapatite. The use of certain calcium or phosphate precursor cement slurry compositions results in a cement which forms the hydroxyapatite in a reliable and quick manner. As mentioned above the resulting hydroxyapatite cement is believed to be biocompatible in contact with hard/soft living tissues. Formation of hydroxyapatite from the calcium salt, calcium oxide, calcium silicate, and calcium phosphate cement slurries is greatly accelerated by the use of inventive solutions that result in an increase of cationic and anionic components i.e. phosphate, chlorine, and calcium ions concentration and/or increase of the pH of the composition, when mixed with cement powder to form a slurry composition. Hydroxyapatite is very low soluble in a wide range of solution pH, ranging approximately from 4 to 14, while within this pH range, other calcium-phosphate compounds have the tendency to dissolve and precipitate as hydroxyapatite. In the pH range of 10 to 14, hydroxyapatite is at its most stable phase. As the cement powder mixes with the water-base solution with high pH or phosphate/calcium ions concentration, the cement setting reactions proceed, pH of the mixture increases till the approximate range of 10 to 14, and a more soluble calcium salt, calcium oxide, calcium silicate, and calcium phosphate compounds begin to dissolve while hydroxyapatite crystals precipitate. The formation of hydroxyapatite and dissolution of the calcium compounds is actually one of the factors responsible for the cement hardening. The ratio of liquid component to powder compartment is in a range of 20 to 100 weight percent.

According to one embodiment herein, the solutions are phosphate buffer saline solution (PBS). PBS is a buffer solution commonly used in biochemistry. It is a salty solution containing sodium chloride, sodium phosphate and potassium phosphate. The solution is isotonic so ions concentration usually matches the human body fluids. The solution has many uses because it is isotonic and nontoxic. After mixing the cement powder with PBS solution, PBS provides an additional source of phosphate ions ($-PO_4$) and increase the phosphate concentration in cement slurry and facilitate and accelerate the chemical reactions of $-PO_4$ with soluble calcium ions ($Ca^{2+}$) of the mixture to form hydroxyapatite crystals.

According to another embodiment, one or more phosphate or calcium in the water base solutions are generally very reactive with respect to hydroxyapatite crystal formation, thereby promote the rate of the crystal formation and reduce the hardening time of the cement. When the solution is at a higher pH, the phosphate and calcium compounds are highly soluble in the water. The phosphate/calcium compounds act as "seeds" that promote and enhance the hydroxyapatite formation rate, there is an increase in the precipitation rate of phosphate/calcium compounds and formation of reactive particles that provide a growth template from which hydroxyapatite crystals form.

According to another embodiment herein, salt water based solutions with cationic and anionic components where the anionic components form strong calcium complexes or insoluble salts and free calcium in the solution. Suitable solutions include sodium fluoride, sodium lactate, sodium acetate, calcium chloride, potassium oxalate and the like. When the solutions are mixed with a calcium salt, calcium oxide, calcium silicate, and calcium phosphate powder, in the case of calcium phosphate components low level amount, the concentration of the free form of the anionic components and the free calcium in the solution is decreased because of their precipitation. Correspondingly, the concentration of phosphate in the solution increases so that the electro-neutrality in the solution is maintained. An increased concentration of phosphate accelerates hydroxyapatite formation and rapid cement setting reactions.

Depending on the type of particular application, various amounts of water-base solution may be utilized to form the cement composition i.e. up to 100%. Sufficient amount of the solution is added to the cement to give it a creamy consistency. In using the preferred cement composition as a root-end filling material, the solution content of the mixture is in the range of 20 to 60 weight percent.

For most of the clinical applications, a cement hardening time more than 60 minutes is too long. Additionally, if the cement sets too rapidly, the time of cement manipulation and placement into the tooth cavity, root canal(s), or bone defect site may not be sufficient. The setting time rate is adjusted for various final uses, and may be rapid if desired. According to various embodiments herein, the final medical/dental biomaterial composition have a hardening time of not more than about 50 (preferably no more than 30) minutes.

In addition to good enough sealing ability, the compositions of the embodiments herein are biocompatible, antibacterial, sterilizable, nontoxic, non-mutagenic, non-carcinogenic, radiopaque, impervious to moisture, and do not provoke any adverse immune response. In various medical/dental treatment procedures, these properties are ideal for repair or generation/regeneration of the surrounding cementum, dentine, bone, and soft tissues.

The composition and the method of use for the same is practical for a wide range of potential indications and clinical applications in medicine and dentistry and both. Potential indications include, but are not limited to: an intermediate filling (liner or base), a direct/indirect pulp capping or pulpotomy (vital pulp therapy) agents, a root canal filling or sealing, a root-end filling, a root perforation repair, a bone cement, grafting, or substitute, and implant materials.

FIG. 1 is a longitudinal view of a healthy mandibular molar tooth showing two roots, a normal pulp and root canals. FIG. 1 shows a longitudinal section of a healthy lower molar tooth with crown, roots, enamel, dentine, cementum, periodontal ligament, alveolar bone, pulp tissue, and the root canals. In a living tooth, the pulp cavity and root canals are filled with fine connective tissue that contains blood vessels, nerves and specific cells. Dentine is the peripheral dress of the pulp and is continuously formed by odontoblast cells throughout the life. The dentin of crown and root areas is covered by a layer of enamel and cementum, respectively.

Figure 2:
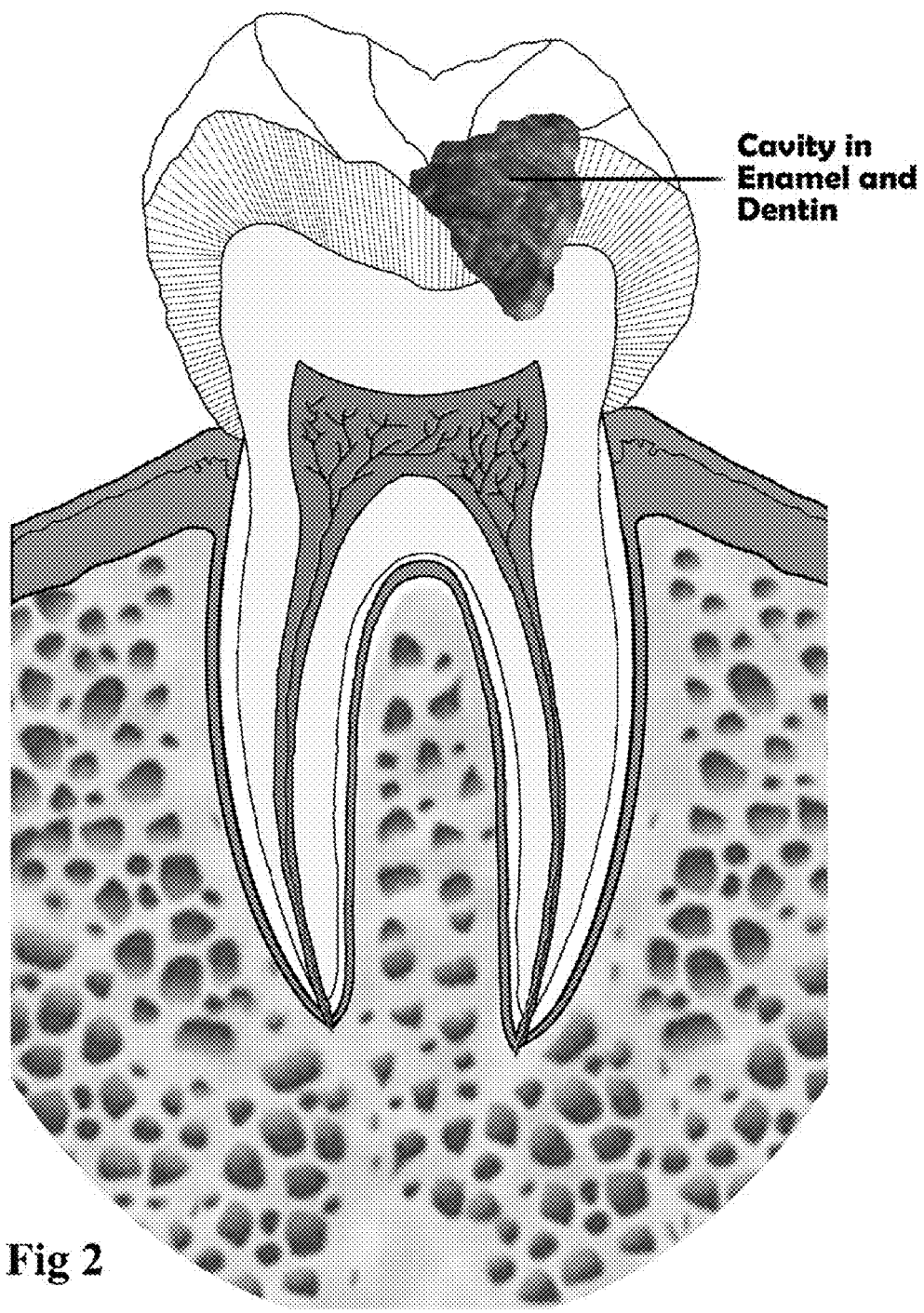
FIG. 2 is a longitudinal view of the tooth of FIG. 1 in which decay has penetrated through the enamel and dentin, according to an embodiment herein.

FIG. 2 is a longitudinal view of the tooth of FIG. 1 in which decay has penetrated through the enamel and dentin, according to an embodiment herein. With respect to FIG. 2, the tooth is damaged and decay has penetrated through the enamel and dentin. Such a tooth needs to be treated with a simple method.

Figure 3:
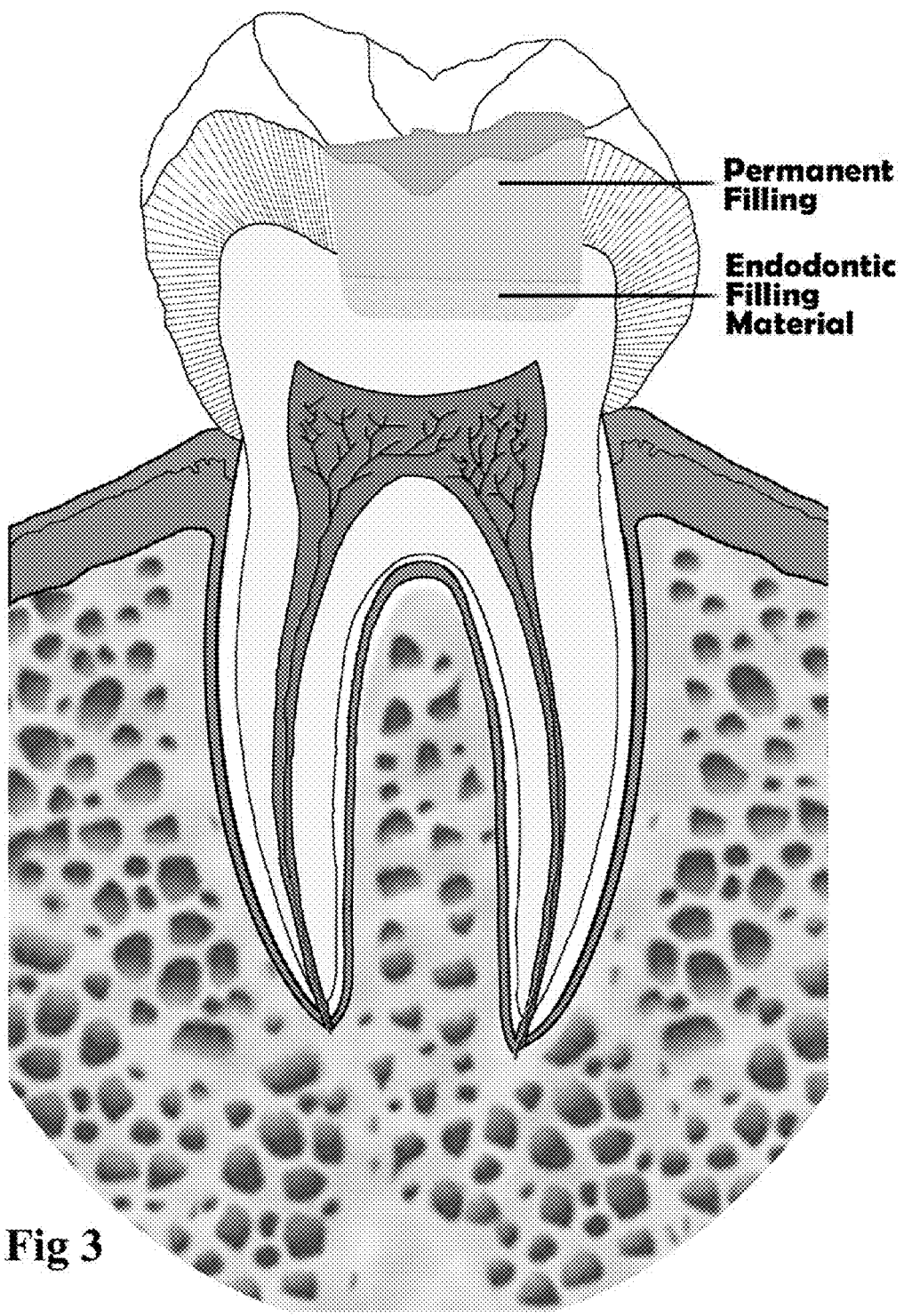
FIG. 3 is a longitudinal view of the same tooth in FIG. 2 in which decay has been removed and the dental biomaterial has been used as an indirect pulp capping agent or an intermediate filling or base for a permanent filling material, according to an embodiment herein.

FIG. 3 is a longitudinal view of the same tooth in FIG. 2 in which decay has been removed and the dental biomaterial has been used as an indirect pulp capping agent or an intermediate filling or base for a permanent filling material, according to an embodiment herein. With respect to FIG. 3, the decay is removed by the following method: the cavity identified and prepared, the inventive dental biomaterial mixed, transferred, inserted, the base of the prepared cavity is filled and sealed as an indirect pulp capping or intermediate filling material or base, and the remaining part of the cavity is filled with another permanent filling material.

Figure 4:
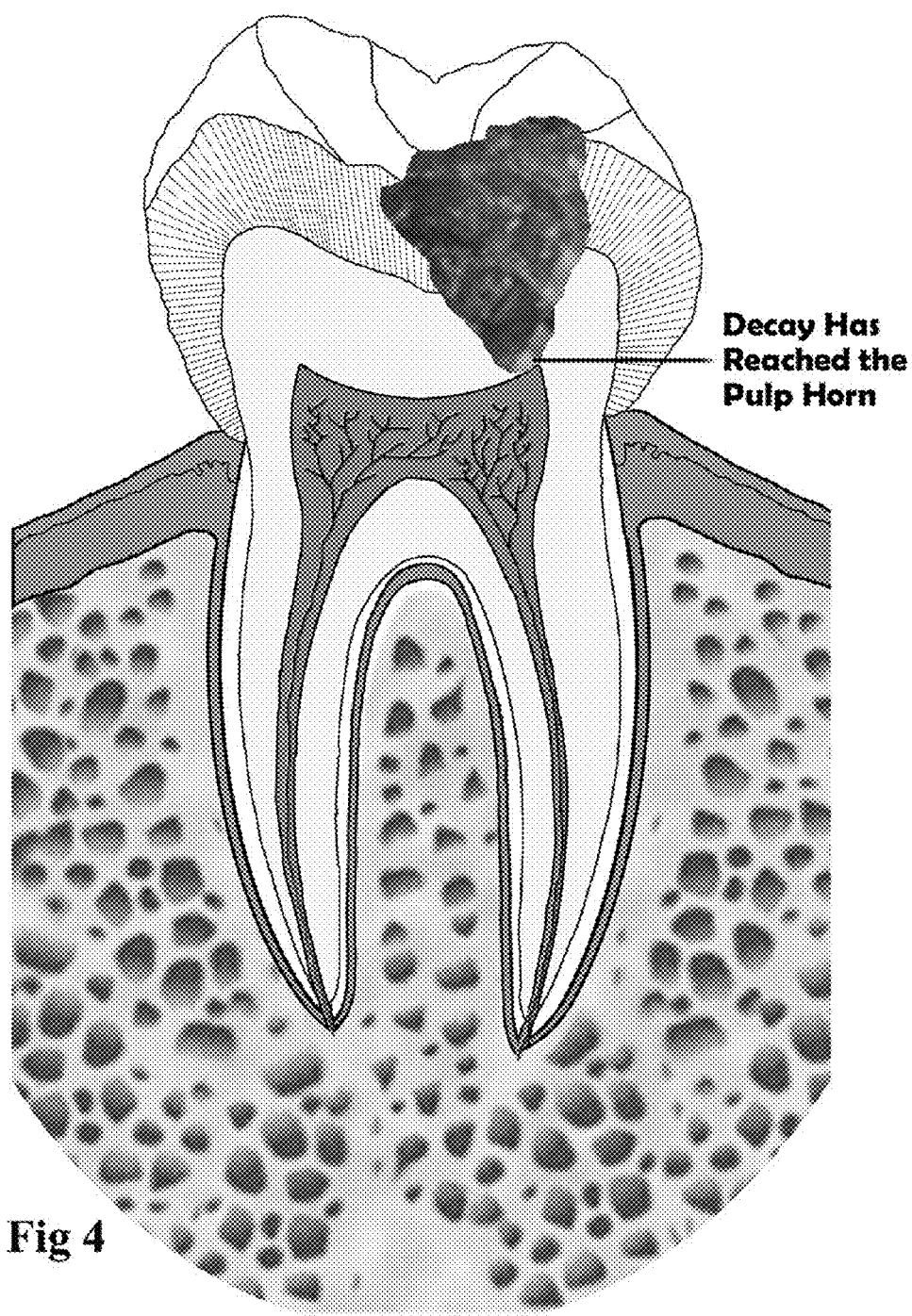
FIG. 4 is a longitudinal view of the tooth of FIG. 1 in which a decay has reached the pulp, according to an embodiment herein.

FIG. 4 is a longitudinal view of the tooth of FIG. 1 in which decay has reached the pulp, according to an embodiment herein. With respect to FIG. 4, a damaged tooth in which decay has penetrated through the enamel and dentin, and probably reached the pulp horn is observed.

Figure 5:
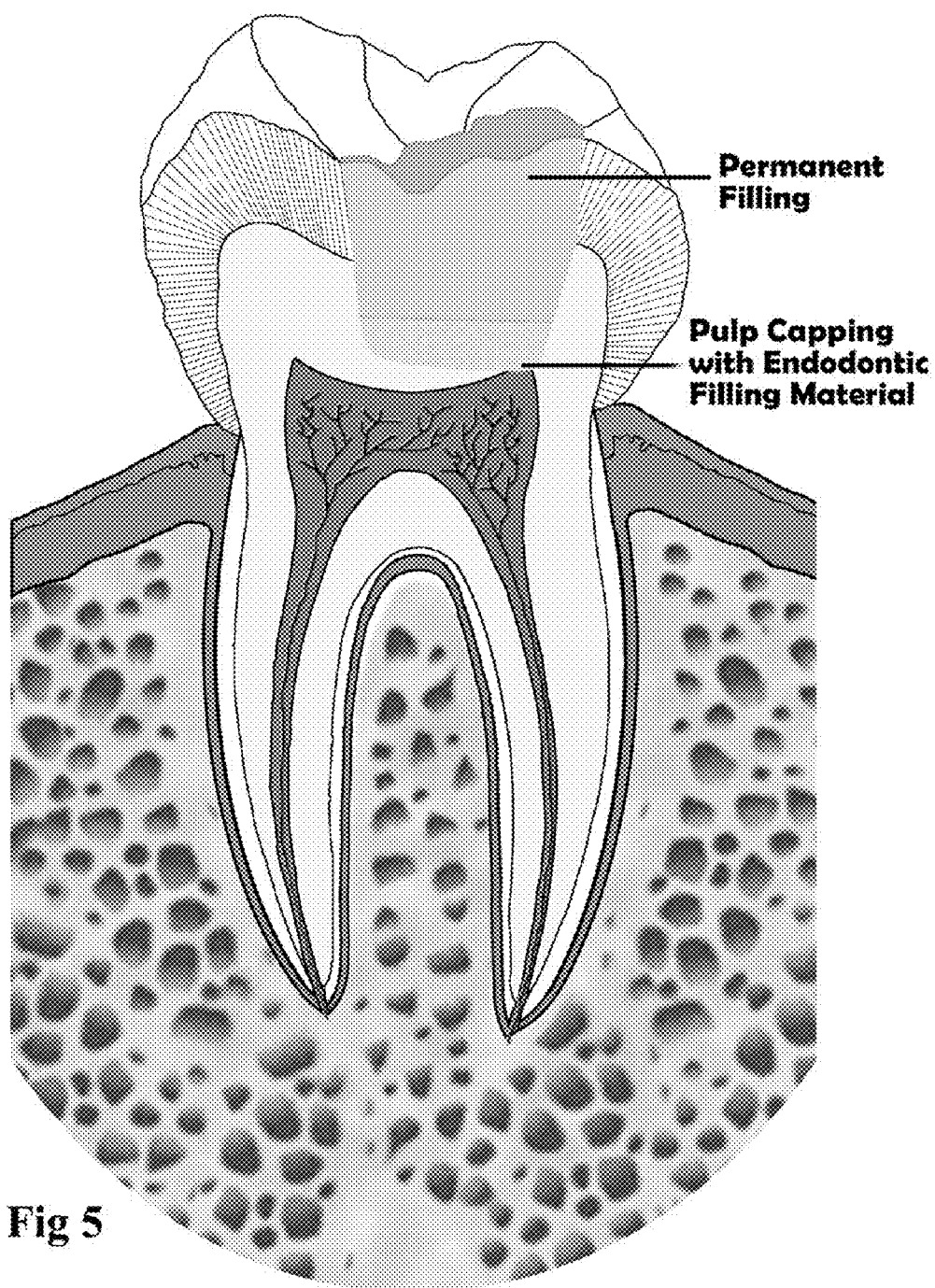
FIG. 5 demonstrate a longitudinal view of the tooth of FIG. 4 in which decay has been removed, the dental biomaterial has been used as a direct pulp capping agent, and a permanent filling has been inserted, according to an embodiment herein.

FIG. 5 shows a longitudinal view of the tooth of FIG. 4 in which decay has been removed, the dental biomaterial has been used as a direct pulp capping agent, and a permanent filling has been inserted, according to an embodiment herein. With respect to FIG. 5, the vital pulp therapy application methods or pulp capping or pulpotomy are accomplished in a simple procedure. The procedure is as follows: the decay has to be removed, and in the case of the pulp exposure during cavity preparation, the pulp bleeding is controlled, the inventive dental biomaterial is mixed, transferred, inserted, and the pulp exposure is capped, the base of the prepared cavity is filled and sealed, and finally the remaining parts of the cavity are filled with the permanent filling material.

When an exposure of the pulp occurs, the powder and liquid are mixed to form a vital pulp therapy agent just before the use, and the compound is then inserted into the exposed site. A surprising finding of this procedure, during direct pulp capping, was a high degree of pulpal vitality and dentinal bridge formation when the inventive dental biomaterial was utilized by its particular method of use.

Figure 6:
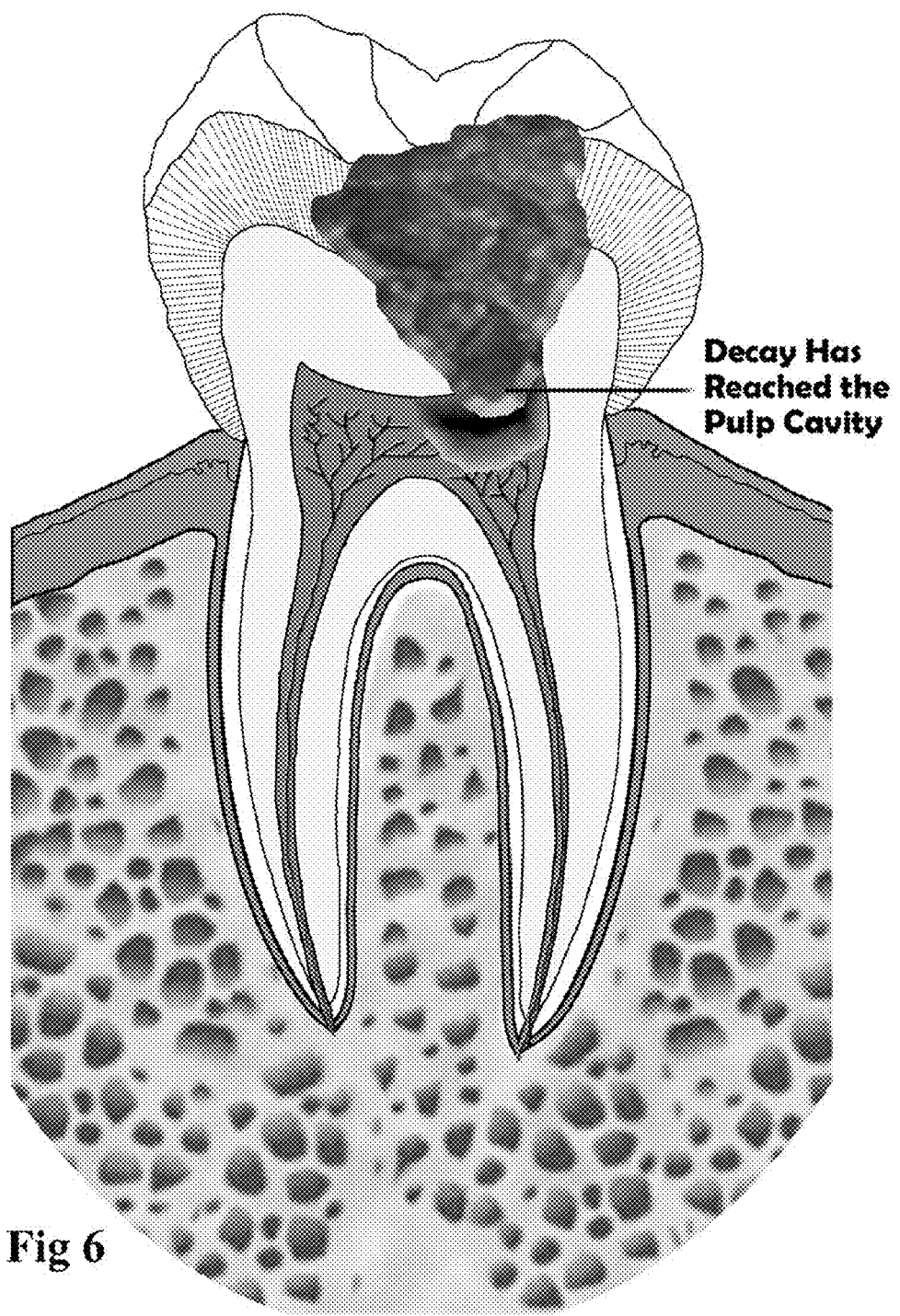
FIG. 6 is a longitudinal view of the tooth shown in FIG. 1 in which decay has reached and damaged the coronal pulp partially, according to an embodiment herein.

FIG. 6 is a longitudinal view of the tooth shown in FIG. 1 in which decay has reached and damaged the coronal pulp partially, according to an embodiment herein. With respect to FIG. 6, the decay has penetrated through the enamel and dentin, reached the pulp, and partially damaged the coronal pulp. Such a tooth needs to be treated.

Figure 7:
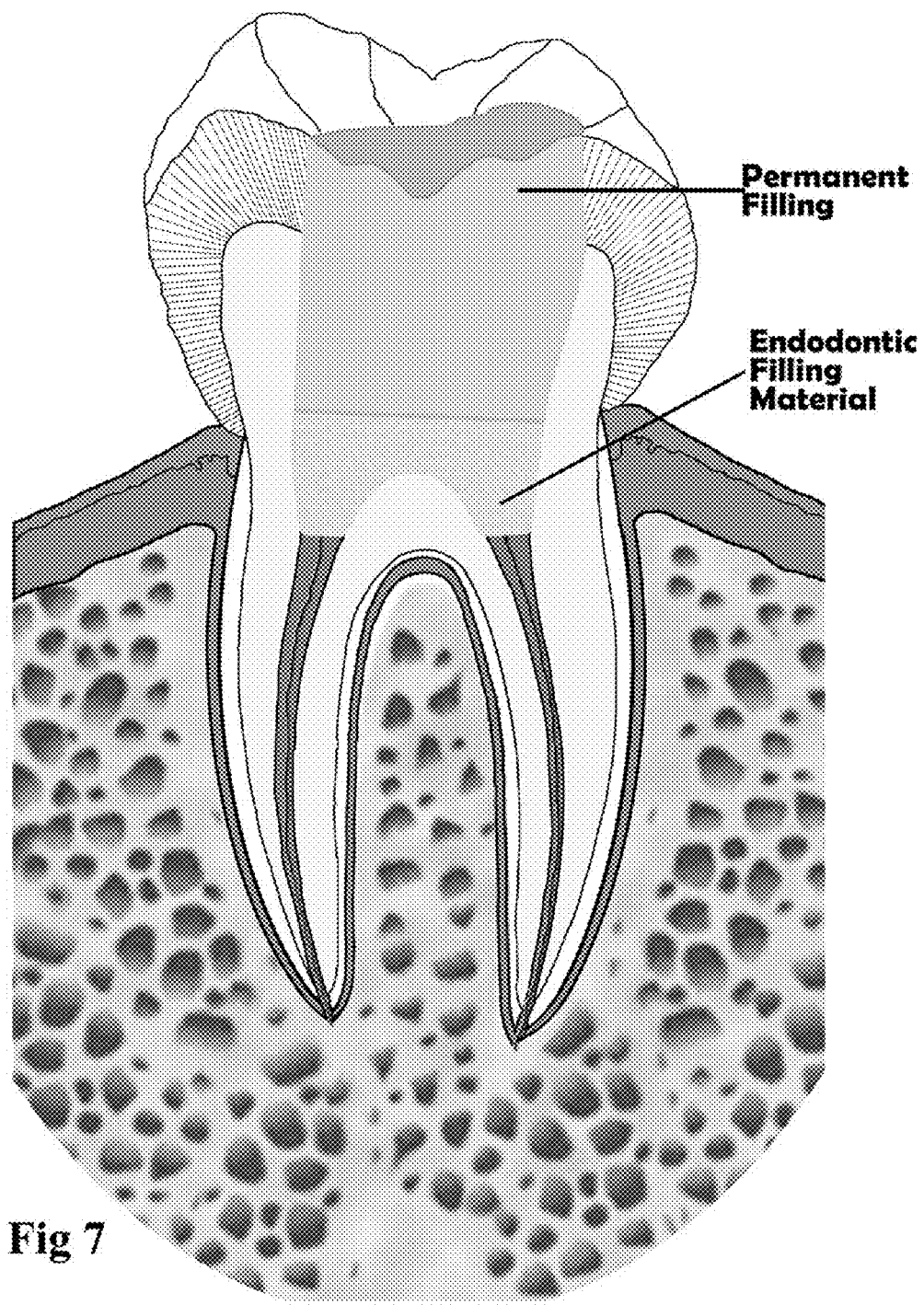
FIG. 7 is a longitudinal view of the tooth of FIG. 6 in which decay has been removed, pulpotomy procedure has been done and the dental biomaterial has been used as a pulpotomy agent, and a permanent filling has been inserted, according to an embodiment herein.

FIG. 7 is a longitudinal view of the tooth of FIG. 6 in which decay has been removed, pulpotomy procedure has been done and the dental biomaterial has been used as a pulpotomy agent, and a permanent filling has been inserted, according to an embodiment herein. With respect to FIG. 7, the tooth is treated with the method. The method is as follows: the decay has been eliminated and the pulp tissue is exposed, the coronal pulp is removed completely/partially, the radicular pulp bleeding has been controlled, the inventive dental biomaterial is mixed, transferred, inserted, and the pulp chamber is filled and sealed, and the remaining parts of the cavity are filled with the permanent filling material.

Figure 8:
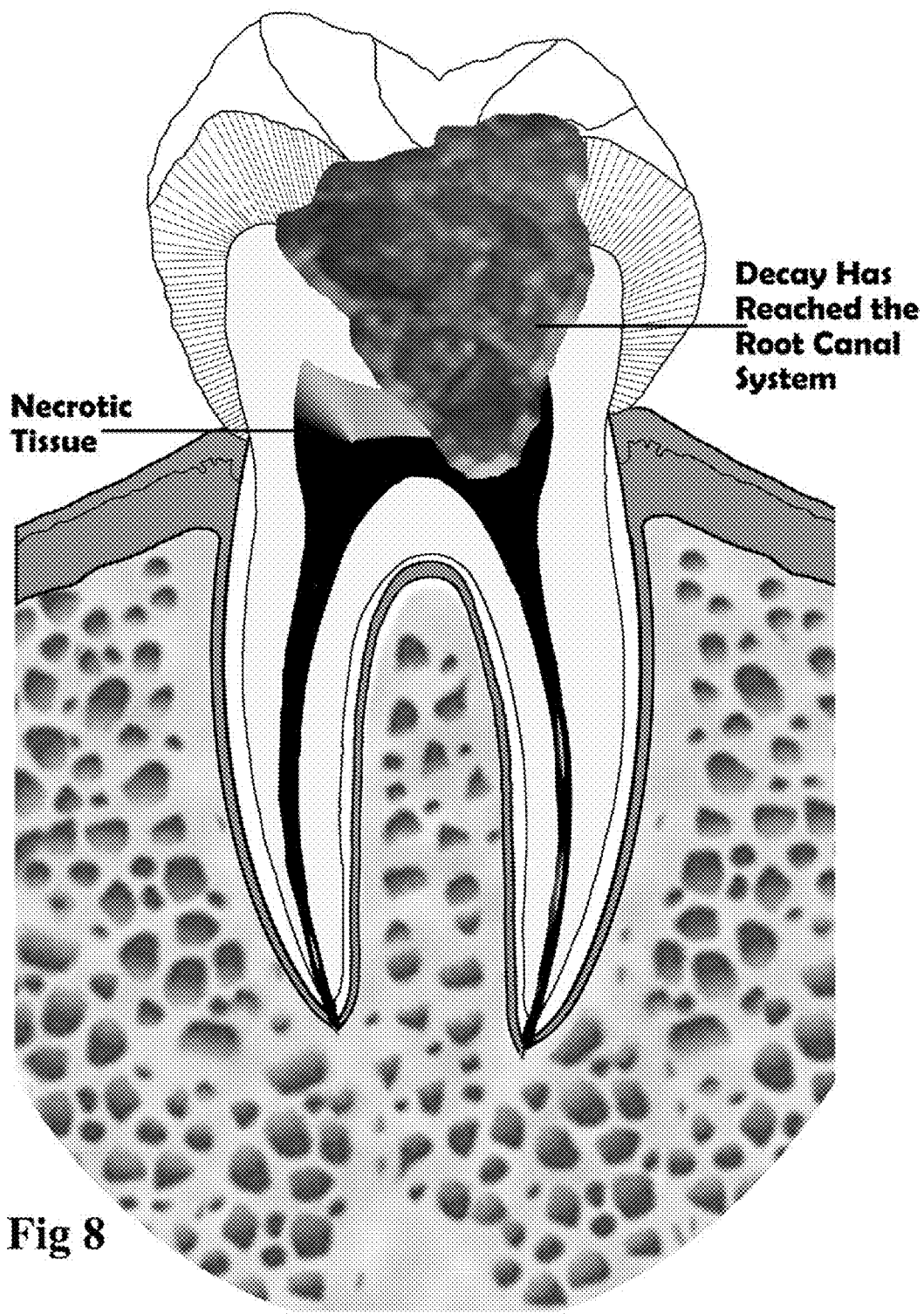
FIG. 8 is a longitudinal view of the tooth of FIG. 1 in which decay has reached and thoroughly damaged the pulp, according to an embodiment herein.

FIG. 8 is a longitudinal view of the tooth of FIG. 1 in which decay has reached and thoroughly damaged the pulp, according to an embodiment herein. With respect to FIG. 8, the decay has penetrated through the enamel and dentin, reached the pulp, and damaged the entire pulp tissue. Such a tooth needs to be treated. The method of treating such tooth is difficult.

Figure 9:
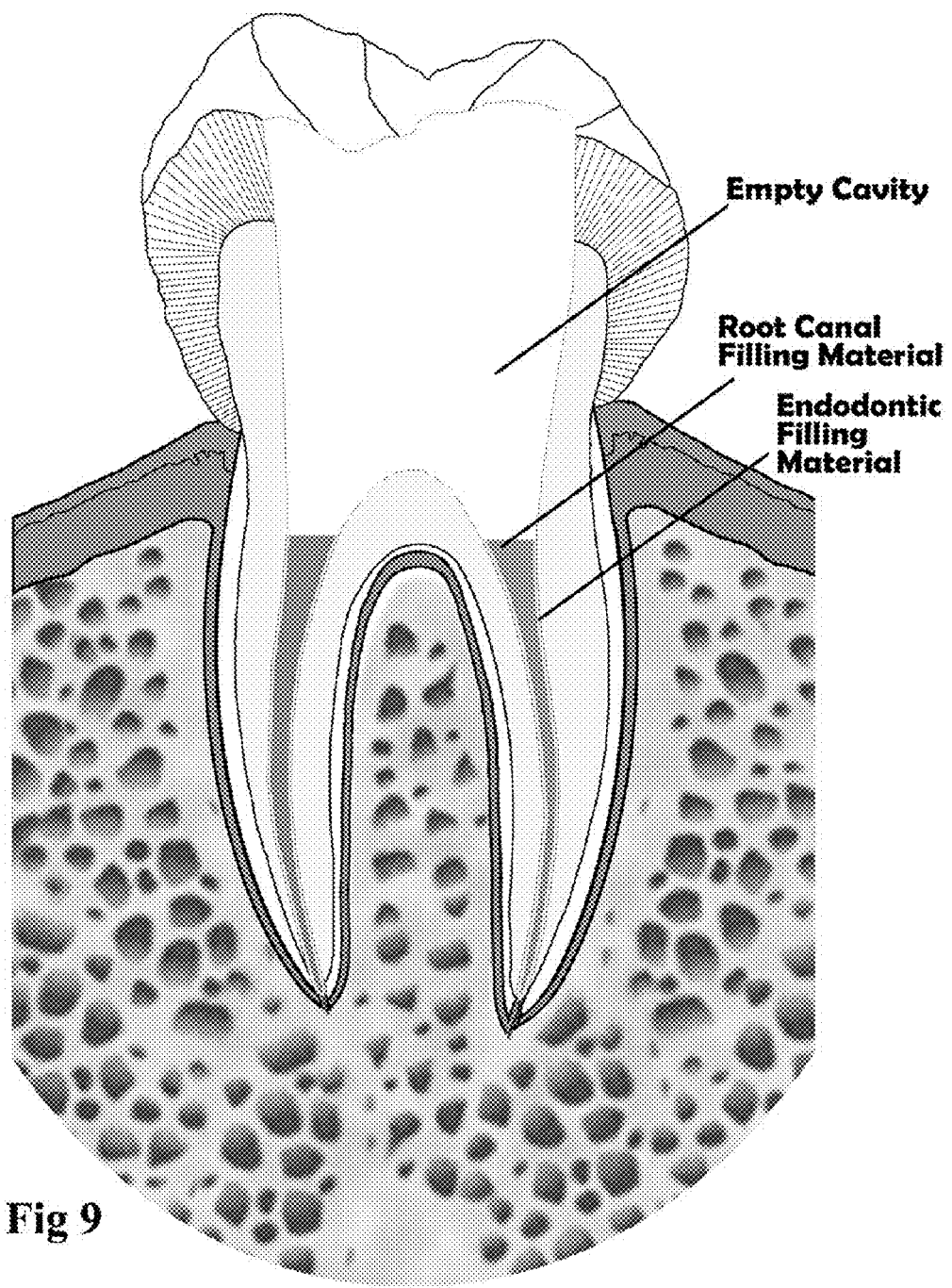
FIG. 9 is a longitudinal view of the tooth of FIG. 8 in which decay has been removed, root canal therapy has been done, and the root canals have been filled with gutta-percha and the dental biomaterial as a root canal sealer, according to an embodiment herein.

FIG. 9 is a longitudinal view of the tooth of FIG. 8 in which decay has been removed, root canal therapy has been done, and the root canals have been filled with gutta-percha and the dental biomaterial as a root canal sealer, according to an embodiment herein. With respect to FIG. 9, the method of treating the tooth is as follows: the decay has been eliminated and the pulp chamber is exposed, using appropriate instruments and root canal procedures the entire damaged or necrotic pulp, microorganisms, and their by-products is removed, and root canal system has been shaped and cleaned, a most common root canal filling material i.e. gutta-percha is used, the inventive dental biomaterial is mixed, transferred, inserted, and the gap is sealed between gutta-percha and root canal walls.

Figure 10:
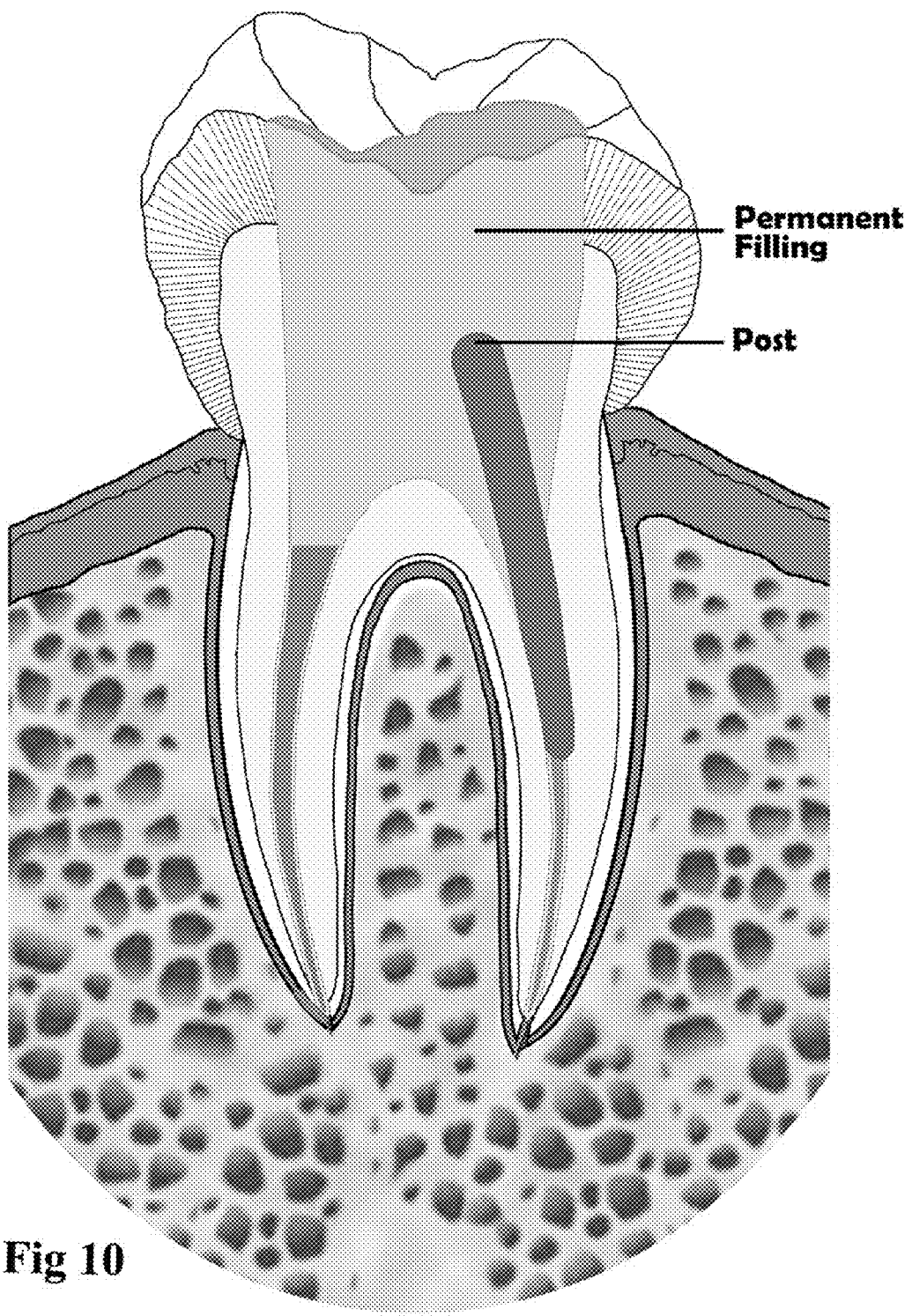
FIG. 10 is a longitudinal view of the tooth of FIG. 9 in which using prefabricated post a permanent filling was done, according to an embodiment herein.

FIG. 10 is a longitudinal view of the tooth of FIG. 9 in which using prefabricated post a permanent filling was done, according to an embodiment herein. With respect to FIG. 10, a longitudinal view of a treated tooth in which endodontic treatment i.e. a root canal therapy (RCT), fabricated/prefabricated intra-canal post cementation, and permanent coronal filling treatments is succeeded. The supporting periodontal ligament (PDL) and bone are healthy. All the treatments were successful.

According to one embodiment, a method of hard tissue induction of dental tissues for promoting tissue generation/regeneration i.e. pulp revitalization, dentinogenesis, and cementogenesis comprising the steps of identifying a tooth cavity, comprises a standard i.e. Class I to Class VI or non-standard tooth cavity preparation, a pulp chamber (partial/complete pulpotomy), a root canal, a root perforation, a root resorption, an internal/external root resorption, and a root-end cavity, to be filled; preparing the cavity to be filled in the tooth; preparing the biomaterial; applying said biomaterial into the tooth cavity; creating a first seal for said tooth cavity; increasing said first seal by tri-dimensional expansion of said biomaterial; releasing biological active material from said biomaterial; thereby creating an antibacterial environment in said tooth cavity as well as creating a second seal over said first seal via hydroxyapatite formation, thereby promoting tissue generation/regeneration including pulp revitalization, dentinogenesis, and cementogenesis. The preferred site for restoration in an endodontic surgery is a root-end cavity.

Figure 11:
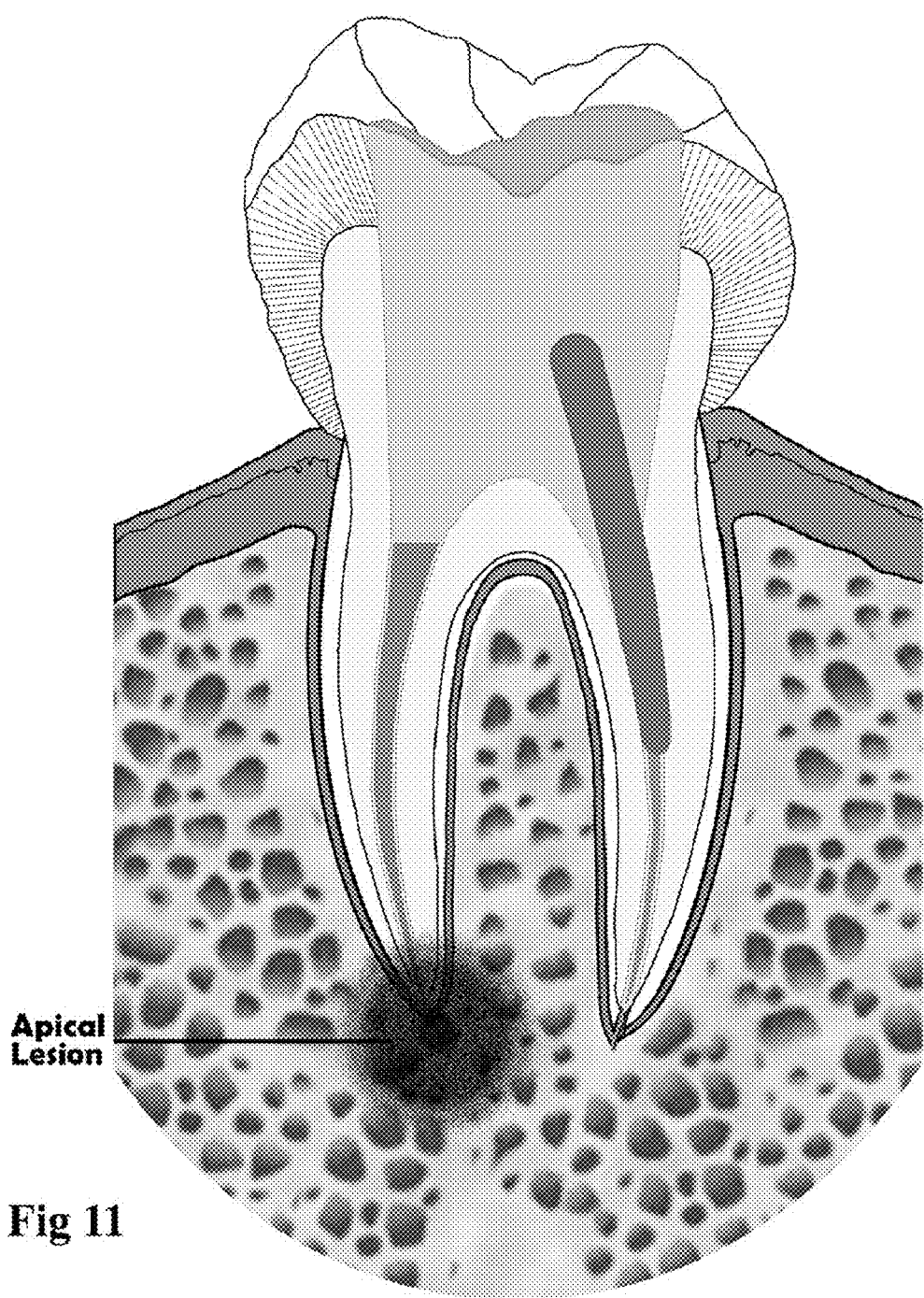
FIG. 11 is a longitudinal view of the tooth of FIG. 10 in which root canal therapy and restorative treatment has been completed, but RCT has failed and a periapical lesion persists, according to an embodiment herein.

FIG. 11 is a longitudinal view of the tooth of FIG. 10 in which root canal therapy and restorative treatment has been completed, but RCT has failed and a periapical lesion persists, according to an embodiment herein. With respect to FIG. 11, a longitudinal view of a tooth in which root canal therapy was failed and a periapical lesion enclosed the infected root apex. Such a tooth needs to be treated with a complicated surgical method as follows: incision and reflection of overlaying gingiva, osteotomy was done to create an opening window, removing the periapical lesion, root-end resection and root-end cavity preparation, mixing the inventive endodontic filling material, its transferring and insertion by using a suitable carrier, so that it fills and seals the root-end cavity, and suturing the incision to complete the surgery.

Figure 12:
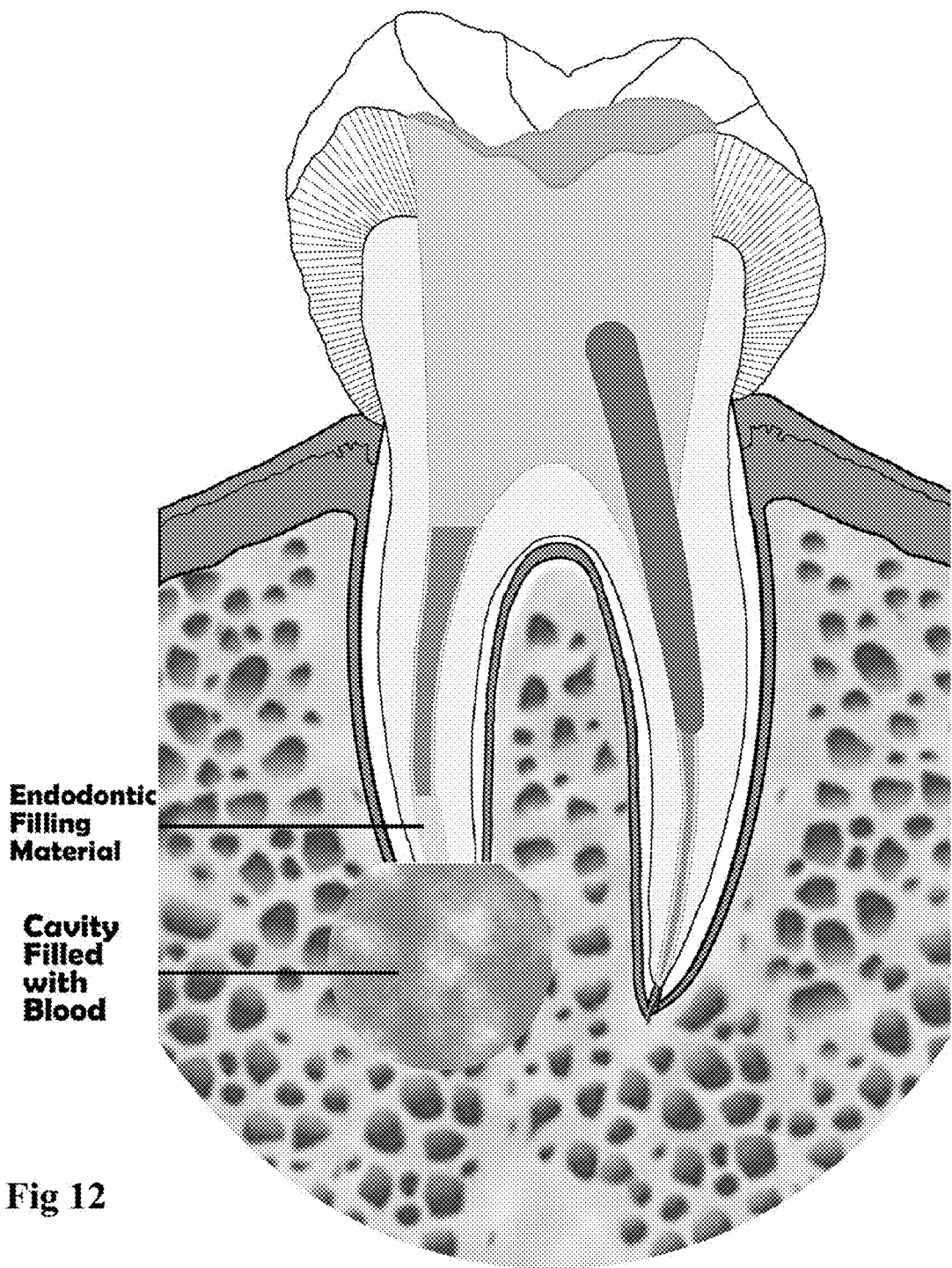
FIG. 12 is a longitudinal view of the tooth of FIG. 11 in which periapical lesion has been removed, periradicular surgery has been completed and root-end filling with the dental biomaterial has been inserted, according to an embodiment herein.

FIG. 12 shows a longitudinal view of the tooth of FIG. 11 in which periapical lesion has been removed, periradicular surgery has been completed, and root-end filling with the dental biomaterial has been inserted, according to an embodiment herein. With respect to FIG. 12, the bone cavity is filled with blood alone. It is well known that surgeons have used a patient's own blood as a vehicle in which to mix the patient's bone chips or bone filler so as to form defect filler. Blood is a useful carrier because it is accessible from the bleeding operative site, is non-immunogenic to the patient and contains BMP which facilitate wound healing through osteogenesis.

Figure 13:
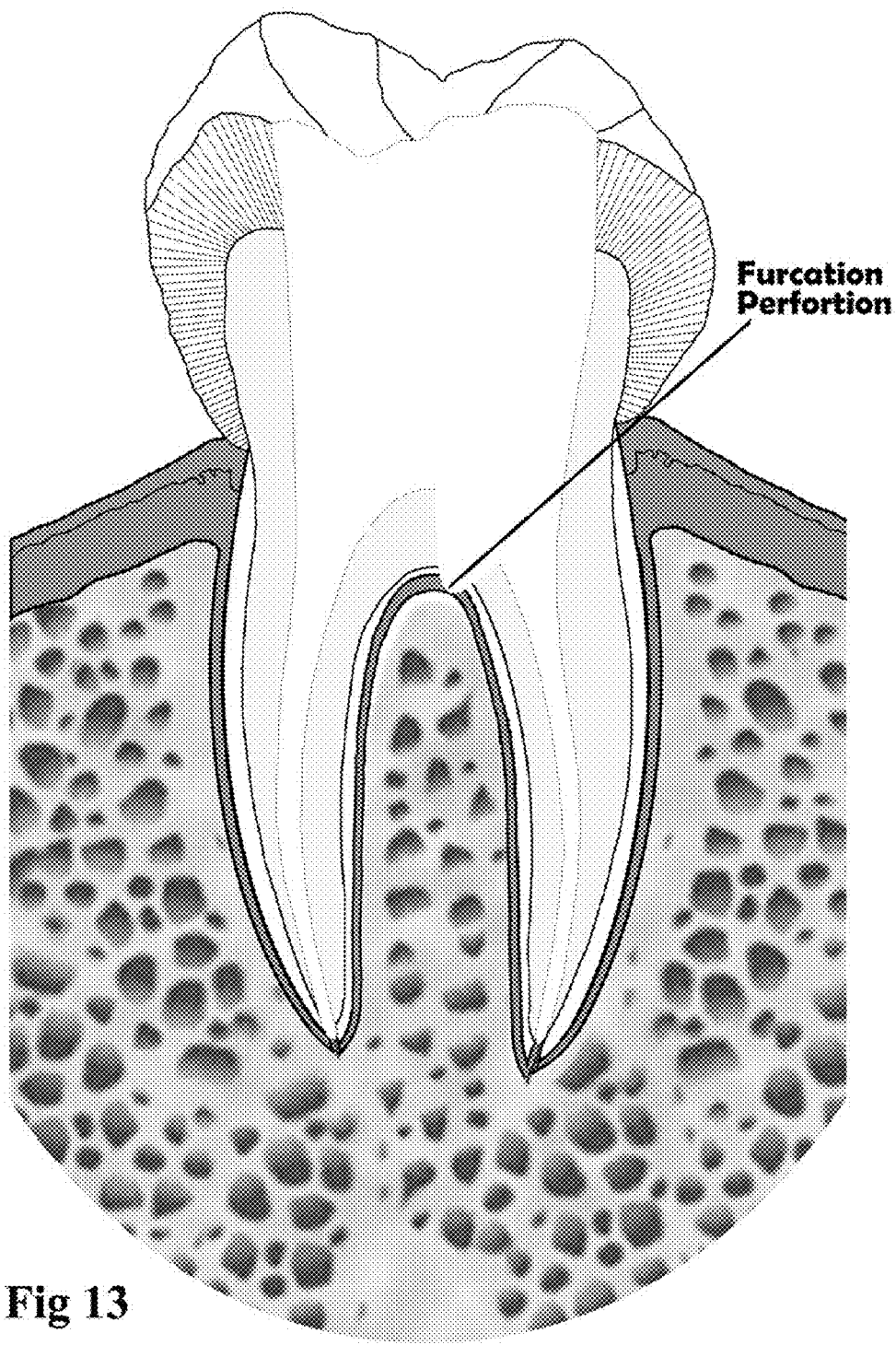
FIG. 13 is a longitudinal view of the tooth of FIG. 1 in which a perforation in the bifurcation has occurred during root canal therapy, according to an embodiment herein.

FIG. 13 is a longitudinal view of the tooth of FIG. 1 in which a perforation in the bifurcation has occurred during root canal therapy, according to an embodiment herein. With respect to FIG. 13, a longitudinal view of a tooth can be seen in which a furcal perforation has been occurred during RCT.

Figure 14:
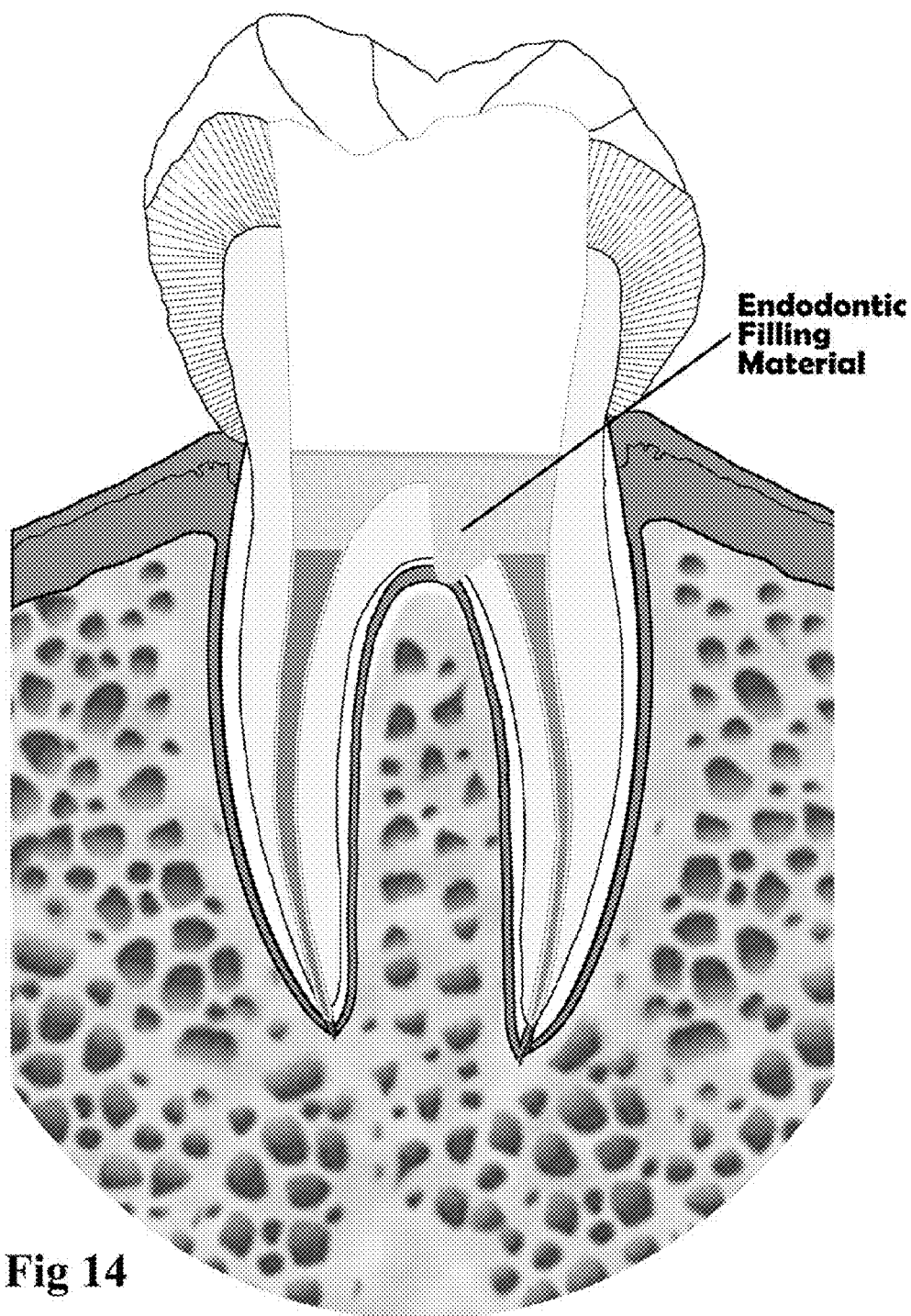
FIG. 14 is a longitudinal view of the tooth of FIG. 13 in which the furcal perforation has been repaired with dental biomaterial after root canal therapy, according to an embodiment herein.

FIG. 14 is a longitudinal view of the tooth of FIG. 13 in which the furcal perforation has been repaired with dental biomaterial after root canal therapy, according to an embodiment herein. With respect to FIG. 14, after RCT the perforation has been repaired with the dental biomaterial.

Figure 15:
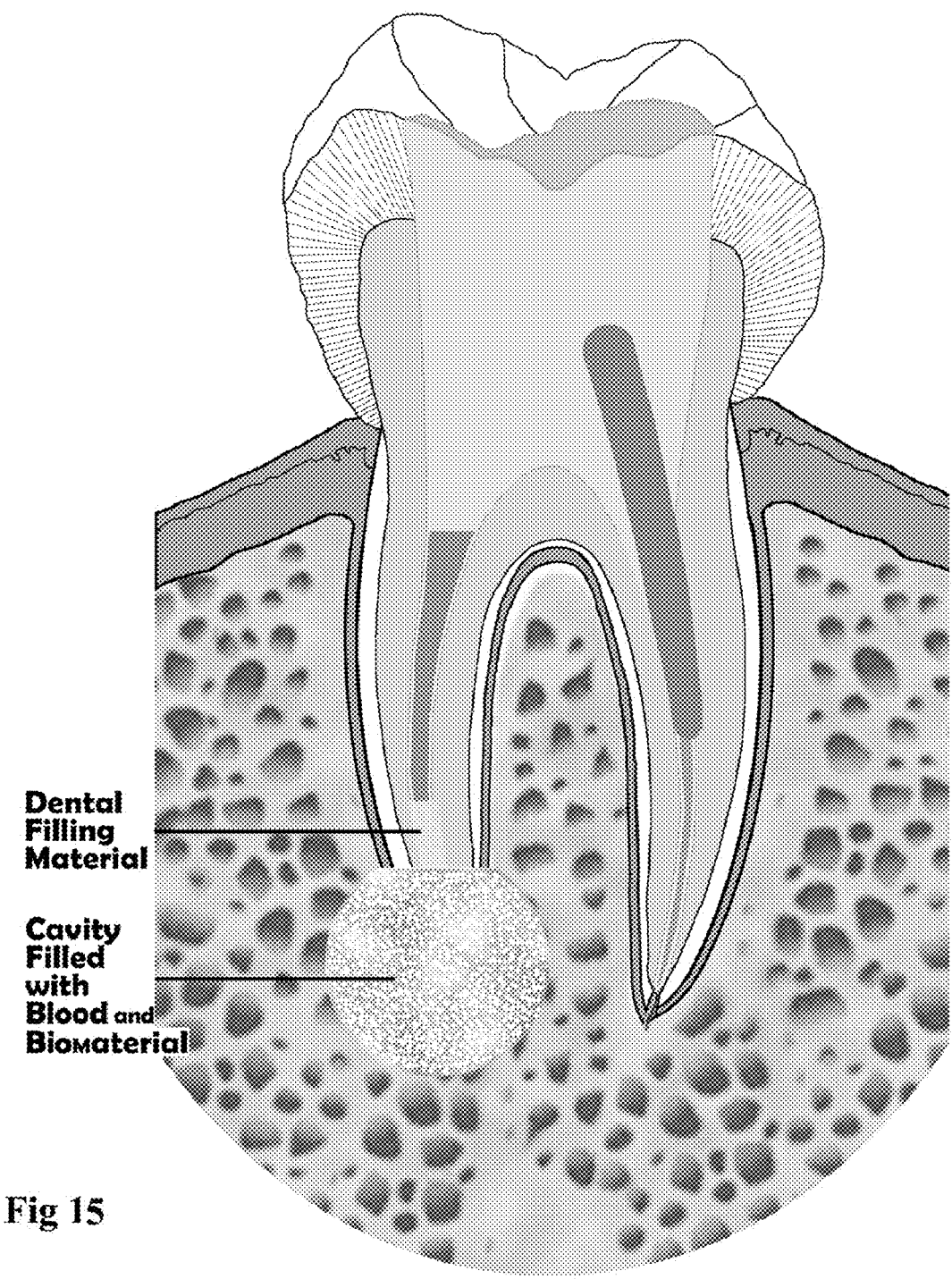
FIG. 15 is a longitudinal view of the tooth of FIG. 11 in which periapical lesion has been removed, periradicular surgery has been completed, bone defect has been filled with the medical biomaterial, and root-end filling with the dental biomaterial has been inserted, according to an embodiment herein.

FIG. 15 is a longitudinal view of the tooth of FIG. 11 in which periapical lesion has been removed, periradicular surgery has been completed, bone defect has been filled with the medical biomaterial, and root-end filling with the dental biomaterial has been inserted, according to an embodiment herein. With respect to FIG. 15, the bone cavity is filled with blood and biomaterial.

According to one embodiment herein, the method of forming a medical biomaterial for hard tissue induction/substitution of bone, comprising the identification and preparation of a site which is going to be restored, repaired, or regenerated in a portion of a bone; and also mixing and applying a composition which consists of preparing a powder component by mixing a plurality of calcium-compound powders; wherein said plurality of calcium-compound powders consist of calcium salt compound powder, calcium oxide compound powder, calcium silicate compound powder, and calcium phosphate compound powder; preparing a liquid component, wherein said liquid is either distilled/deionized water, or water-base salt solutions with alkaline, neutralized or acidic pH; preparing a phosphate and calcium enriched mixture cement, wherein said mixture cement is prepared by mixing said powder component with said liquid component, wherein a ratio of said liquid to said powder is in a range of 20 to 60 weight percent; applying fresh, set, or treated form of said mixture cement either alone, or along with at least an active/non-active additive, in the body adjacent tissue for dental/non-dental hard tissue induction/substitution; and releasing biological active material from said biomaterial for osteoinduction/osteoconduction; thereby promote osteogenesis and said biomaterial is progressively replaced with natural bone.

According to one embodiment herein, the powder component may comprise from 0.5 to 98 weight percent of an active/non-active additive such as Portland and/or calcium-silicate/calcium-aluminate cement. The cement is a bioactive material and mainly consists of tricalcium silicate, dicalcium silicate, tricalcium aluminate, and tetracalcium aluminoferrite. In the presence of an aqueous environment, the biominerals produce a large amount of hydroxyl and calcium ion, which readily alter and raise the pH of the area, and react with phosphate ion of body tissue fluid to form hydroxyapatite crystals. Therefore the biominerals have an excellent biocompatibility. The process for preparing calcium-silicate/calcium-aluminate cement, comprising the steps of homogenizing calcium carbonate, silica, and alumina to produce a mixture having the following proportions: $CaCO_3$ 60-80%, $SiO_2$ 20-35%, and $Al_2O_3$ 1-10% by weight using wet technique; drying the mixture at >100° C. for 24 h; grinding the dried mixture to produce a powder; shaping and compacting the powder in wet form to produce a bulk; melting said bulk at a temperature ranging up to 1650° C. to produce a melt; quenching said melt; grinding the quenched melt to produce a powder, thereby the calcium-silicate/calcium-aluminate cement of the embodiments herein, is free of iron compound and mainly consists of tricalcium silicate, dicalcium silicate and tricalcium aluminate.

According to one embodiment herein, the medical/dental biomaterial includes nano-particles and comprises at least one nano-particle selected from the group consisting of nano-silica, nano-titanium oxide, nano-iron, nano-iron oxide, nano-alumina, nano-zinc oxide, nano-boron, nano-calcium carbonate, nano-clay; nanotubes (e.g. Carbon nanotubes); nanofibers (e.g. carbon nanofibers); nanocomposites (e.g., NCs), and combinations thereof, to develop a biomaterial with high-performance and durability potential and having a range of novel properties such as low electrical resistivity, self-cleaning, self-healing, and self-control of cracks. Nanoparticles have a high surface area to volume ratio, providing the potential for remarkable chemical reactivity; a reduction in particle size can lead to a more rapid reaction, setting and hardening of cement due to stronger electrostatic attractive forces and a greater specific surface. The nano-particles act as nuclei for cement phases, further promoting cement hydration reaction due to their high reactivity, as nano-reinforcement. Additionally, the nano-particles as filler fill the pores and enhance the density of cement to increase strength and these characteristics will improve the microstructure of cement and the interface between the cement and tooth cavities. According to one embodiment, the nano-silica is added to the powder component of the biomaterial. The addition of nano-silica results in significant early increase of compressive strength of cement; the microstructure of the nano-silica added cement is dense, less permeable and uniform. In addition, the nano-silica is also included in the biomaterial composition as a set accelerator to accelerate the setting time of the mixture cement. Generally, the nano-silica is defined as nano-silica having a particle size up to 100 nanometers. The nano-silica is present in the biomaterial in an amount in the range of from about 0.25 to 25 weight percent.

According to another embodiment herein, the medical biomaterial, a method to manufacture the same and the application of the same as surgical implant to fill a bone defect, to augment of the formation of bone tissues, like in the case of the augmentation of alveolar ridges, or to change the form of bone tissue in reconstructive surgery of maxillofacial bones. The biomaterial contains resorbable (biodegradable)/nonresorbable naturally-occurring/synthetic polymer/copolymer material e.g. a hydroxy acids, polyamides, polyesters, polyurethanes, poly(vinyl alcohol), poly(ethylene glycol), pluronic, poly (vinylpyrollidone), cellulose, cellulose acetate, hydroxyethyl cellulose, hydroxypropyl cellulose, carboxymethyl cellulose, poly(ethylene terephthalate), poly(anhydride), poly(propylene fumarate), collagen, fibrin, matrigel, alginate, modified alginate, elastin, chitosan, chitin, gelatin, polylactic acid (PLA) polymer, polyglycolic acid (PGA) polymer, polylactic-co-glycolic acid (PLG/PLGA), poly(D, L-lactic acid) (PDLLA), Poly($\epsilon$-caprolactone) (PCL), polycarbonates, polyesteramides (PEA), poly-p-dioxanone (PDS), poly-beta-hydroxypropionic acid (PHPA), poly-beta-hydroxyvaleric acid (PHVA), glycolide/trimethylenecarbonate copolymer (PGA/TMC), poly-beta-hydroxybutyric acid (PHBA), glycolide/lactide copolymer (PGA/PLA) copolymer, poly(acrylonitrile-co-vinyl chloride), or polylysine, polysulfone, and combinations thereof. According to one embodiment herein, the resorbable (biodegradable) polymer/copolymer material is added to the medical biomaterial. Resorbable polymer/copolymer is organic high-molecular weight materials that are depolymerized in tissue conditions to monomers or oligomers. Resorbable polymer/copolymer is removed from the living tissues by means of the normal metabolism of cells. An advantage of the medical biomaterial having resorbable polymer/copolymer is that the resorbable polymer/copolymers are removed from the living tissues after they have completed their mission without needing a separate removal operation.

According to one embodiment herein, set mixture of medical/dental biomaterial grinds to produce a micro/macro-particles, treated with an aqueous salt solution or blood/blood derivatives containing calcium/phosphate ions to form calcium-phosphate i.e. hydroxyapatite crystal on the surface of the treated set cement. Hydroxyapatite is a component that is useful in biomaterial applications as it is a strong and dense material that mimics natural bone composition and stimulates the generation/regeneration of hard tissues in the body. When hydroxyapatite is formed on the surface of the treated set cement, hard tissue generation/regeneration occurs. Human bones and teeth contain a high percentage of hydroxyapatite. According to one embodiment herein, hydroxyapatite is added as an additive material to the powder component. According to another embodiment, a precursor to hydroxyapatite, tetracalcium phosphate is used as a powder component. When the biomaterial sets, a calcium hydrophosphate is formed that reacts in presence of the tissue body fluid with the tetracalcium phosphate to form hydroxyapatite. According to one embodiment, both hydroxyapatite and precursor to hydroxyapatite is used as powder components.

The medical/dental biomaterial according to the embodiments herein, has advantageous uses for in vitro and in vivo tissue engineering. According to one embodiment herein, the biomaterial provides set cement with or without calcium phosphate crystal, and said set cement treated alone or with third component that comprises of at least one said active/non-active additive material in single/multi phases, to produce a treated set cement in the form of three-dimensional scaffolds/shaped pieces, particulates, fine or coarse free/encapsulated powders, pellets, microspheres, macrospheres, porous, macroporous and microporous structures, compact material, a thin layer/films, granulated form, implantable device, coatings, paste or a prefabricated kit in association with/without biological cells. The three-dimensional scaffolds/shaped pieces have characteristics of degradability, biocompatibility, high surface area/volume ratio, osteoconductivity, mechanical integrity and allowance of cellular deposition. A biocompatible three-dimensional scaffolds/shaped pieces that is degradable over a time scale into non-toxic by-products withdraws in concert with new tissue/bone formation. For improvement of the tissue regeneration, biological cells are incorporated into the three-dimensional scaffolds/shaped pieces prior to, during or subsequent to the production process. Cell adherence is carried out by exposure of the three-dimensional scaffolds/shaped pieces to a population of cells either in vitro or in vivo. Sequential or simultaneous exposure is used.

The following examples give further illustrations of preferred embodiments herein, but are not to be construed as in any way limiting the scope as set forth in the claims.

Example One

The preferred embodiment of the present endodontic filling material in this example has the following powder and liquid compositions:

A) Powder: Tricalcium silicate and dicalcium silicate (61%), barium sulfate (14%), tricalcium phosphate and dicalcium phosphate (8%), calcium sulfate (5%), calcium hydroxide (5%), calcium oxide (2%), calcium aluminate (2%), calcium carbonate (2%), and calcium chloride (1%).

B) Liquid: The liquid was a phosphate buffer saline solution of the following composition: 1.7 g $KH_2PO_4$, 11.8 g $Na_2HPO_4$, 80.0 g NaCl, and 2.0 g KCl in 10 liters of distilled water (pH 7.2).

According to the embodiments herein, the use of the endodontic filling material provided an effective means for pulp capping agents and procedures. In order to determine these capabilities, a study of procedures was done and as follows: a cavity preparation was made in each of the eight animal teeth. During the preparation, exposure of the pulp occurred. Control of bleeding was accomplished with sterile cotton pellet. The dental biomaterial was then mixed on a sterile pad and applied to the exposure site. An appropriate self-curing glass ionomer restorative material was applied to fill the prepared cavity and then it was cured.

When the procedure was conducted in this experiment, the results indicated an extremely high level of remaining pulpal vitality (100%) and a complete dentinal bridge formation over the exposed pulp area (75%) after the procedure. No pulpal inflammatory reaction was noted for the treated teeth.

Example Two

The powder and liquid compositions in this example are as follow:
A) Powder: Tricalcium silicate and dicalcium silicate (48%), tricalcium phosphate and dicalcium phosphate (18%), barium sulfate (15%), calcium hydroxide (6%), calcium sulfate (6%), calcium oxide (3%), calcium carbonate (2%), calcium fluoride (1%), and calcium aluminate (1%).
B) Liquid: The liquid was a normal saline solution of the following composition: 9.0 g NaCl in 1 liters of distilled water.

The performance of the endodontic filling biomaterial with the above composition was evaluated for root-end filling using dye penetration method. This method of measuring the sealing ability of root-end filling materials is well known. In dye penetration test, the root-end cavity was first prepared and then filled with the biomaterial to be tested. The dye penetration test allows a comparison between the sealing ability of standard filling materials, such as MTA, and the cement composition of the embodiments herein. After coating the outside of the tooth with nail varnish in order to prevent dye leakage from anywhere except the cavity that is being tested, the tooth was immersed in dye solution. The tooth was then sectioned and examined under light microscopy, and the degree of dye leakage along cavity walls was measured.

The procedure of such a test was as follows: Sixty-six extracted single rooted human teeth were cleaned, shaped, and obturated in the same method. Nail varnish was then applied to the entire external surface of each root and was allowed to be dried. Three to four millimeters of the apical segment of each root was removed at a 90 degree angle to the longitudinal axis of the root. The resected surface was acid etched, and a thin layer of pit and fissure sealant was applied to prevent dye penetration through the exposed dentinal tubules. After that, a 3 mm deep root-end cavity was ultrasonically prepared. The samples were randomly divided into 3 test groups, each having 20 roots. Six roots were used as positive and negative control groups. Samples were filled with the described prepared biomaterial to be compared with commercially available formulations of IRM (Caulk Dentsply, Milford, Del., USA), and mineral trioxide aggregate (ProRoot MTA, Dentsply Tulsa Dental, Tulsa, Ok., USA). After a day the samples were totally immersed in aqueous solution of methylene blue for 24 hours. Roots were sectioned longitudinally into two halves and the extent of leakage along cavity walls was then observed under the stereomicroscope. The results of the study, expressed in millimeters, are reported.

These results in the case of sealing the retrograde cavities, demonstrated the mean microleakage of the dental biomaterial (0.785±0.763 mm) less than IRM (2.675±0.922 mm) and MTA (0.985±0.914 mm), while the statistical difference for these two comparisons was significant and non significant, respectively. Positive and negative controls responded as expected. ANOVA test showed statistically significant differences among experimental groups (P<0.001), but Tukey's test revealed no significant difference between the dental biomaterial of the embodiment herein and MTA as the gold standard. It was concluded that the sealing ability of the dental (endodontic) biomaterial of the embodiments herein and MTA is the same and superior to IRM. Although direct application and relevance of such dye leakage studies to clinical practice has been questioned, such tests are the oldest and easiest method to test new dental materials. Furthermore, when the filling material does not allow penetration of small molecules such as those exhibited in the dye it has a logical potential to prevent leakage of large molecules such as bacteria and/or by-products.

Example Three

The powder and liquid compositions in this example are as follow:
A) Powder: Tricalcium silicate and dicalcium silicate (40%), tricalcium phosphate (20%), barium sulfate (18%), calcium sulfate (8%), calcium oxide (6%), calcium carbonate (4%), calcium hydroxide (3%), and calcium fluoride (1%).
B) Liquid: The liquid was a phosphate buffer saline solution of the following composition: 1.7 g $KH_2PO_4$, 11.8 g $Na_2HPO_4$, 80.0 g NaCl, and 2.0 g KCl in 10 liters of distilled water (pH 7.2).

Based on the embodiments herein, the use of the endodontic filling material, provided an effective additional seal, second seal, for the most outer area of the root-end filling material and the surrounding dentin, via its ability of hydroxyapatite crystal formation, so that a hydroxyapatite cap blocked the communication path between root canal system and periradicular area by its adhesion to the material and surrounding dentine and both.

The study design for the evaluation of this ability was as follows: ten extracted single rooted human teeth were cleaned, shaped, and obturated with gutta-percha in the same method of the second example. Three millimeters of the apical segment of each root was removed. A root-end cavity preparation was made ultrasonically in each tooth. The described prepared material was then mixed and inserted into the root-end cavity. The samples were totally immersed in normal saline solution for 5 months in room temperature. The presence of hydroxyapatite cap was then observed under the scanning electron microscope (SEM).

The results showed that the hydroxyapatite cap was formed over the inventive root-end filling material and surrounding dentine, while the boundary gap between them was sealed by hydroxyapatite crystals. The nature of these crystals was determined by electron probe microanalysis (EPMA) and the results were comparable with standard hydroxyapatite.

Example Four

The compositions of the powder and liquid in this example are as follow:
A) Powder: Tricalcium silicate and dicalcium silicate (36%), barium sulfate (18%), tricalcium phosphate (12%), calcium sulfate (9%), silica (6%), calcium oxide (6%), calcium hydroxide (6%), calcium carbonate (4%), calcium aluminate (2%), and calcium chloride (1%).
B) Liquid: The liquid was a salt solution of the following composition: 8.0 g sodium fluoride and 4.0 g calcium hydroxide in 1 liters of distilled water.

According to the embodiments herein, the use of the medical/dental biomaterial provided an antibacterial effect against the invasive microorganisms. It was reported that MTA as a root-end filling material and calcium hydroxide as a successful intracanal dressing material have the reasonable antibacterial property. Using agar diffusion test, the antibacterial effect of the inventive medical/dental biomaterial is evaluated and compared with MTA and calcium hydroxide and the both.

The design of this study was as follows: a 5 millimeter holes were punched in the sterilized agar. MTA, calcium hydroxide (according to manufacturers' instruction), and the inventive medical/dental biomaterial were then prepared and inserted into the holes. A second layer of agar with a polymicrobial mixture was added and they were stored in the room temperature for 2 hours. The plates were incubated at 37 degree Celsius for 72 hours. The inhibition zones of bacterial growth were measured at 24, 48, and 72 hours.

The results indicated that the mean diameter of inhibition zones detected around the inventive medical/dental biomaterial was remarkably greater than the ones found for MTA and comparable with calcium hydroxide. Using ANOVA test demonstrated that the difference among these three test groups was statistically significant. However, using paired test in order to compare the inventive medical/dental biomaterial with MTA and calcium hydroxide showed significant and non significant differences, respectively.

Example Five

The compositions of the powder and liquid in this example are as follow:

A) Powder: Calcium silicate (0.5%), barium sulfate (14%), tricalcium phosphate (10%), calcium sulfate (2%), calcium oxide (0.5%), zirconium oxide (2%), zinc oxide (2%) and calcium-silicate/calcium-aluminate cement (69%), wherein the process for preparing calcium-silicate/calcium-aluminate cement, comprising the steps of homogenizing calcium carbonate, silica, and alumina to produce a mixture having the following proportions: $CaCO_3$ 65-75%, $SiO_2$ 25-30%, and $Al_2O_3$ 2-5% by weight using wet technique; drying the mixture at >100° C. for 24 h; grinding the dried mixture to produce a powder; shaping and compacting the powder in wet form to produce a bulk; melting said bulk at a temperature ranging up to 1650° C. to produce a melt; quenching said melt; grinding the quenched melt to produce a powder.

B) Liquid: The liquid was a phosphate buffer saline solution of the following composition: 1.7 g $KH_2PO_4$, 11.8 g $Na_2HPO_4$, 80.0 g NaCl, and 2.0 g KCl in 10 liters of distilled water (pH 7.2).

The performance of the dental biomaterial with the above composition was evaluated for pulpotomy/vital pulp therapy of a molar tooth with established irreversible pulpitis. Following diagnostic examination, pulpotomy of the first mandibular molar was planed. A 0.2% chlorhexidine rinse was carried out. The tooth was anesthetized, isolated and then caries was completely excavated; the entire coronal pulp tissue was removed with a sterile bur with water spray. The remaining radicular pulp vitality was confirmed by the presence of both blood and pulp tissue. Hemorrhage was controlled with sterile cotton pellets; a thick layer of dental biomaterial was placed with gentle pressure to cover the remaining radicular pulp stump. The permanent restoration was then completed with amalgam.

Six, twelve, and 24 months follow-ups revealed no clinical or radiographic pathological findings i.e. inflammation, infection, calcification, and resorption on the treated molar; tooth mobility was within the normal physiological range and patients were asymptomatic. In addition, radiographs showed normal periodontium apparatus; an evidence of complete periapical healing.

Example Six

The production of porous microspheres of medical biomaterial in this example is as follow:

A) Powder component: Calcium silicate (0.5%), barium sulfate (14%), tricalcium phosphate (10%), calcium sulfate (2%), calcium oxide (0.5%), zirconium oxide (2%), zinc oxide (2%) and calcium-silicate/calcium-aluminate cement (69%).

B) Liquid component: The liquid was a phosphate buffer saline solution of the following composition: 1.7 g $KH_2PO_4$, 11.8 g $Na_2HPO_4$, 80.0 g NaCl, and 2.0 g KCl in 10 liters of distilled water (pH 7.2).

C) Preparation of porous microspheres of medical biomaterial: The process for preparing treated set cement, comprising the steps of: mixing the powder component and liquid component; storing the mixture at 37° C. incubator and 95% humidity for 24 hour to set; drying the set mixture at >100° C. for 24 hour; grinding the dried set mixture to produce a powder; storing the powder in the water base solution at 37° C. incubator up to 7 day to produce treated powder with precipitation of a calcium-phosphate i.e. hydroxyapatite; removing and drying the treated powder with hydroxyapatite from the solution; dissolving a resorbable (biodegradable)/nonresorbable naturally-occurring/synthetic polymers/copolymers in a solvent i.e. chloroform to produce a solution; adding the dry treated powder with hydroxyapatite to the solution; adding camphene to the solution to produce a composite solution; adding the composite solution into a water bath containing alcohol while stirring to promote solidification, thereby harden new microspheres due to the solvent evaporation and to introduce pore channels assisted by the sublimation of camphene; washing the new microspheres thoroughly with ice-cooled distilled water using an appropriate filter; freeze-drying the new microspheres; obtaining the porous microspheres of medical biomaterial for clinical use.

The performance of the porous microspheres of medical biomaterial with the above characteristics was evaluated as bone substitute during periradicular surgery of a maxillary incisor. Clinical and radiographic examinations showed sign/symptoms of chronic apical periodontitis. The surgical field was locally anesthetized. A full-thickness flap was incised and raised. The periradicular inflammatory lesion was then circumferentially detached from the bony crypt and teeth; it was then removed. Root-end filling was done according to current technique with the endodontic filling biomaterial of the embodiments herein. Afterwards, the bone defect was filled with the obtaining porous microspheres of medical biomaterial and the patient blood. The flap was then positioned and sutured with monofilament suture.

The sutures were removed seven days later and soft tissue healing was observed; the healing proceeded uneventfully.

Five months following the bone surgery there were no clinical sign and or symptoms of inflammation, tenderness to percussion or palpation, reports of pain or discomfort, mobility, sinus tract formation and periodontal pocket formation. Radiographic examination revealed the almost complete resorption of medical biomaterial as bone substitute and subsequent osteogenesis and bone replacement via osteoconductivity and osteoinductivity mechanisms at the follow up session.

Example Seven

The compositions of the powder and liquid in this example are as follows:

A) Powder: Tricalcium silicate and dicalcium silicate (70%), barium sulfate (4%), tricalcium phosphate (4%), calcium sulfate (4%), calcium oxide (0.5%), zirconium oxide (6%), zinc oxide (4%), nano-silica (0.5%), and tricalcium aluminate (7%).

B) Liquid: The liquid was a simulated body fluid (SBF) solution of the following composition: 7.996 g NaCl, 0.350 g $NaHCO_3$, 0.224 g KCl, 0.228 g $K_2HPO_4$ ($3H_2O$), 0.305 g $MgCl_2$ ($6H_2O$), 40 mL 1 $kmol/m^3$HCl, 0.278 g $CaCl_2$, 0.071 g $Na_2SO_4$, and 6.057 g $(CH_2OH)_3CNH_2$ in 750 mL of ultra-pure water.

The performance of the dental biomaterial with the above composition was evaluated pulp revitalization of a necrotic open apex tooth. After local anesthesia with 2% lidocaine and 1:80000 epinephrine and isolation, the caries were completely removed and an appropriate access cavity was prepared. The root canal was passively irrigated with 20 mL of full strength NaOCl during 20 min. Root canal was dried and a creamy paste of triple antibiotics was placed to sterilize the environment and the tooth temporarily restored. Three weeks later, the tooth again anesthetized, isolated, and the temporary restoration removed. The triple antibiotic paste omitted from the root canal using 10 mL irrigation of full strength NaOCl/canal; the root canal was dried with paper points. Apical tissue was stimulated using a K-file. Bleeding started and blood filled the canal. After 10 min, fast setting dental biomaterial was placed over the canal orifice, and gently adapted to dentinal walls using a moistened cotton pellet. After that the tooth was restored.

Three, six, and twelve months follow-ups were carried out. The tooth was clinically functional with no clinical signs/symptoms. Radiographic examinations revealed that the immature root was fully developed due to pulp revitalization.

The use of the dental biomaterial provides many advantages over prior filling or sealing dental materials. The novel biomaterial is compatible with the hydrophilic environment of mouth and provides an acceptable setting in the presence of moisture or blood. The moisture of mouth not only adversely affects the biomaterial, but also such moisture actually plays an important role in the chemical reactions responsible for better sealing and hardening process. Such nature of the biomaterial leads to better wetting, penetrance, filling, and sealing, so that more easy manipulation and use in the moisty environment of mouth or bone is gained. This is particularly important when this biomaterial is used for root-end filling where the blood flow is often difficult to control. The embodiments herein provide a means for formulating the cement in such a way that the cement can be easily prepared, transformed, placed, filled and the tooth cavity or bone cavity can be completely sealed. The biomaterial does not show any shrinkage during its setting, while it has an expansion when it is used in a moist or wet field. Formation of hydroxyapatite in addition to all above can be mentioned as one of the final products of chemical reactions for the biomaterial according to the embodiments herein. The biomaterial has a good adaptation with tooth cavity walls, hardens within a desired time, and has resistance against being washed out. Finally a tooth with an unchanged color can be detected. In the presence of excess biomaterial during tooth filling process, it is easy to remove it. The novel dental biomaterial has a good adaptation to dentinal walls and improved sealing ability. Providing a more complete seal of the tooth cavity or root canal greatly increases the ability of resistance from the ingress of liquids into the filled cavity or root canal system. Such liquids, if allowed to enter a cavity or root canal, may introduce microorganisms and their by-products capable of re-infecting the tooth and surrounding bone or tissues. The inventive biomaterials and methods in comparison with the conventional ones improve the ability of sealing the root canal system resulting in yielding a tooth more resistant to microbial leakage. According to common dye penetration method for measuring the effectiveness of root-end filling materials' seal, the novel endodontic filling biomaterial of the preferred embodiment of the invention outperforms both IRM and MTA cements which are currently used in practice.

According to the embodiments herein, the novel medical or dental biomaterial contains antimicrobial agents such as calcium hydroxide and calcium oxide that reduce the existence of microorganisms and neutralize their by-products. In addition, by raising the pH value during the setting process, the material according to the embodiments herein, gives an extra antimicrobial effect in sealing areas that reduces the possibility of infection or further decay of the tooth structure. It is also sterilized easily. The medical or dental biomaterial in the embodiments herein is bioactive and biocompatible that favorably allows dental and bone tissues healing and regeneration. The bioactive particles in the cement composition are characterized by their ability to form hydroxyapatite i.e. the principal mineral in teeth and bones, and also stimulation and promotion of tissue repair and regeneration in contact to living dental and bone tissues. This is particularly important when it is in direct contact with the exposed or damaged pulp, periapical tissues or bone. The bioactive composition therefore find a particular utility to seal cavities in a wide variety of dental or medical treatments that require a filling or sealing biomaterial such as pulp capping or pulpotomy agent, root canal sealant, root canal filling, root-end filling, implant material, bone cement and as perforation repair compositions.

What can be implied from various above descriptions and drawings of the medical/dental biomaterial and the method of its use, is that various features can be used single or in any combination thereof. Therefore, this invention is not necessarily restricted to the preferred embodiments depicted herein. In addition, it should be known that variations and modifications within the field of the invention may occur to those skilled in the art to which the invention pertains. Therefore, the present invention may utilize in other specific forms without departing from its spirit or essential characteristics.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the appended claims.

Although the embodiments herein are described with various specific embodiments, it will be obvious for a person skilled in the art to practice the invention with modifications. However, all such modifications are deemed to be within the scope of the claims.

It is also to be understood that the following claims are intended to cover all of the generic and specific features of the embodiments described herein and all the statements of the scope of the embodiments which as a matter of language might be said to fall there between.

What is claimed is:

1. A method for soft and hard tissue healing, generation and regeneration using a medical and dental biomaterial comprises:
    identifying an appropriate dental or a non-dental tissue as a site for an insertion of said biomaterial;
    preparing said insertion site for said biomaterial in said identified dental or non-dental tissues, wherein said insertion site is prepared by removing a decay;
    preparing a powder component by mixing a plurality of calcium-compound powders; wherein said plurality of calcium-compound powders consists of calcium salt compound powder (A), calcium oxide compound powder (B), calcium silicate compound powder (Aa), and calcium phosphate compound powder (Ab), and wherein an amount of said calcium oxide compound powder (B) is 8-15 percent by weight, and wherein an amount of said calcium silicate compound powder (Aa) is within 47-71 percent by weight, and wherein an amount of said calcium phosphate compound powder (Ab) is within 9-24 percent by weight and ratio of (Ab)/(Aa) is between 13-50 percent;

adding a liquid component, wherein said liquid component is selected from a group consisting of distilled water, deionized water, normal saline, phosphate buffer saline (PBS) solution, simulated body fluid (SBF) solution, blood and blood derivatives, water-base salt solutions and wherein a pH of said water base salt solutions is alkaline or neutral or acidic pH;

preparing a phosphate ($PO^4$) and calcium ($Ca^{2+}$) enriched cement mixture for dental or medical use, wherein said cement mixture is prepared by mixing said prepared powder component with said prepared liquid component thereby producing fast setting, antibacterial cement and hydroxyapatite and wherein a ratio of said prepared liquid component to said prepared powder component is within a range of 20 to 60 weight percent; and applying said cement mixture in a body adjacent tissue for inducing and substituting a dental or non-dental soft and hard tissue to induce a healing and a generation and regeneration of said soft and hard tissue and wherein said cement mixture is applied fresh or wherein said cement mixture is applied in a set or wherein said cement mixture is applied in a treated form or wherein said cement mixture is applied alone or wherein said cement mixture is applied along with at least an active additive or wherein said cement mixture is applied along with at least a non-active additive, wherein said healing and generation and regeneration of soft and hard tissue includes a process selected from a group comprising of an osteogenesis, a dentinogenesis, a cementogenesis, a pulp revitalization processes, and combinations thereof at said site.

2. The method as claimed in claim 1, wherein said calcium salt compound powder is selected from a group comprising of calcium sulfate, calcium carbonate, calcium aluminate, calcium lactate, calcium nitrate, calcium citrate, calcium acetate, calcium stearate, calcium fumarate, calcium malate, calcium chloride, calcium bromide, calcium fluoride, calcium iodide, calcium saccharate, calcium oxalate, calcium gluconate, calcium propionate, calcium caseinate, calcium glycerophosphate, and combinations thereof.

3. The method as claimed in claim 1, wherein said calcium oxide compound powder is selected from a group comprising of calcium oxide, calcium peroxide, calcium hydroxide, and combinations thereof.

4. The method as claimed in claim 1, wherein said calcium silicate compound powder is selected from a group comprising of tetracalcium silicate, tricalcium silicate, dicalcium silicate, monocalcium silicate, amorphous calcium silicate and combinations thereof.

5. The method as claimed in claim 1, wherein said calcium phosphate compound powder is selected from a group comprising of octacalcium phosphate, heptacalcium phosphate, pentacalcium phosphate, tetracalcium phosphate, tricalcium phosphate, dicalcium phosphate, monocalcium phosphate, calcium pyrophosphate, calcium metaphosphate, calcium phosphinate, amorphous calcium phosphate, calcium hydroxide phosphate and combinations thereof.

6. The method as claimed in claim 1, wherein said at least an active additive is selected from a group comprising of therapeutic materials, bioactive molecules, biomaterials, biominerals, hydroxyapatite, bioactive calcium phosphate, antibiotics, medicaments, antibacterial agents, anti-viral agents, cariostatics, anti-inflammatory agents, anti-oxidants, organic and mineral fraction of bones and teeth, biologic factors, bioactive substances and cells, drugs, proteins, hormones, enzymes, antigens, immunogens, cytotoxins, neurotransmitters, interferons, interleukins, chemokines, cytokines, extracellular matrix components, ligands and peptides, osteoinductive factors, and combinations thereof, and wherein at least a non-active additive is selected from a group comprising of gutta-percha, latex, gelling agents, adhesives, crystal adjustors, viscosity modifiers, preservatives, plasticizers, pore forming agents, fibers and meshes, metals, oxides, bone chips, bone crystals, polymeric resins, resorbable and biodegradable and nonresorbable and naturally-occurring and synthetic polymers and copolymers, synthetic peptide containing powder, adhesion molecules, nano-particles, nanotubes, nanofibers, and combination thereof.

7. The method as claimed in claim 1, wherein said powder component and said liquid component are further added with one or more active additives or one or more non-active additives, wherein said one or more active additives are selected from a group comprising of therapeutic materials, bioactive molecules, biomaterials, apatite, hydroxyapatite, oxyapatite, apatite fluoride, fluorine-hydroxylapatite, carbonated hydroxyapatite, bioactive calcium phosphate, antibiotics, medicaments, antibacterial agents, anti-viral agents, cariostatics, anti-inflammatory agents, anti-oxidants, organic and mineral fraction of bones and teeth, biologic factors, bioactive substances, drugs, proteins, hormones, enzymes, antigens, immunogens, cytotoxins, neurotransmitters, interferons, interleukins, chemokines, cytokines, extracellular matrix components, ligands and peptides, osteoinductive factors, and combinations thereof and wherein one or more non-active additives are selected from a group comprising of filler materials, radiopaque materials, minerals, biominerals, bioceramics, bioglass, bioactive and biocompatible glass ceramics, Portland cement, calcium-silicate and calcium-aluminate cement, silica, fumed silica, amorphous silica, silicate glass, alpha-whitlockite, beta-whitlockite, lithium silicate, glass fiber, quartz, fluoride preparation, gutta-percha, latex, gelling agents, alkaline earth metal silicate crystals, pigments/dyes, adhesives, crystal adjustors, viscosity modifiers, preservatives, plasticizers, pore forming agents, fibers/meshes, metals, zinc oxide, zirconia, alumina, zirconia-alumina ceramic, bismuth subcarbonate, tin oxide, titania, bone chips, bone crystals, polymeric resins, resorbable and biodegradable and nonresorbable and naturally-occurring and synthetic polymers and copolymers, synthetic peptide containing powder, adhesion molecules, nano-particles, nanotubes, nanofibers, and combination thereof.

8. The method as claimed in claim 1, wherein a concentration of said calcium salt compound powder, calcium oxide compound powder, calcium silicate compound powder, calcium phosphate compound powder, and an active additive or non-active additive in the biomaterial is within 0.5 to 98 percent by weight.

9. The method as claimed in claim 1, wherein a ratio of said liquid component to said powder component is within a range of 20 to 100 weight percent.

10. The method as claimed in claim 1, wherein said powder component is prepared in a particulate form and wherein said powder component is prepared in a fibrous form and wherein a size of the powdered component is selected from a group comprising of a nanosized particle, a microsized particle, a macrosize particle, and mixtures thereof, and wherein said powder component and said liquid component are mixed to produce a mixture, wherein said mixture is treated in single phase alone or wherein said mixture is treated in multi phases alone or wherein said mixture is treated in single phase with a third component or wherein said mixture is treated in multi phases with a third component and wherein said third component comprises of at least one said active additive material or wherein said third component comprises a non-active additive material and wherein said mixture is treated to produce a treated set cement in a form and wherein said form is selected from a group comprising of a three-dimensional scaffold and shaped pieces, particulates, a fine and coarse free encapsulated powders, a pellets, microspheres, macrospheres, a porous structure, a macroporous structure, a microporous structures, a compact material, a thin layer, a thin film, granulated form, an implantable device, a coating, a paste and a prefabricated kit in association with and without cells.

11. The method as claimed in claim 10, wherein said three-dimensional scaffolds and shaped pieces are osteoconductive and osteoinductive.

12. The method as claimed in claim 1, wherein said mixture is ground to produce microparticles and wherein said mixture is ground to produce a macro-particles, wherein said micro particles and said macro-particles contact with a solution to obtain a precipitate of calcium and phosphate on a surface of said micro particles and said macro-particles and wherein said precipitate of calcium and phosphate is hydroxyapatite crystal and wherein said micro particles and said macro-particles are removed from said solution and wherein said solution is selected from a group comprising of an aqueous salt solution, a blood and a blood derivative containing calcium and phosphate ions, wherein said aqueous salt solution and said blood and said blood derivative containing calcium and phosphate ions act as a biomaterial covered with calcium-phosphate.

13. The method as claimed in claim 6, wherein said resorbable and biodegradable polymer or copolymer material is selected from a group consisting of poly(ethylene glycol), poly(propylene fumarate), polylactic acid (PLA) polymer, polyglycolic acid (PGA) polymer, polylactic-co-glycolic acid (PLG/PLGA), poly(D,L-lactic acid) (PDLLA), Poly(e-caprolactone) (PCL), polycarbonates, polyesteramides (PEA), poly-p-dioxanone (PDS), poly-beta-hydroxypropionic acid (PHPA), poly-beta-hydroxyvaleric acid (PHVA), glycolide/trimethylenecarbonate copolymer (PGA/TMC), poly-beta-hydroxybutyric acid (PHBA), and glycolide/lactide copolymer (PGA/PLA), and wherein nonresorbable polymer or copolymer consists of poly(acrylonitrile-co-vinyl chloride), and wherein naturally occurring polymer or copolymer is selected from a group consisting of cellulose, collagen, fibrin, matrigel, alginate, elastin, chitosan, chitin, and gelatin, and wherein the synthetic polymer or copolymer is selected from a group consisting of hydroxy acids, polyamides, polyesters, polyurethanes, poly(vinyl alcohol), pluronic, poly(vinylpyrollidone), cellulose acetate, hydroxyethyl cellulose, hydroxypropyl cellulose, carboxymethyl cellulose, poly(ethylene terephthalate), poly(anhydride), modified alginate, polylysine, and polysulfone.

14. The method as claimed in claim 7, wherein a process of preparing a powder comprising calcium-silicate and calcium-aluminate cement comprises:
homogenizing a calcium carbonate, a silica, and an alumina to produce a mixture using a wet technique and wherein a ratio of the calcium carbonate ($CaCO_3$) in said mixture is within 60-80% by weight and wherein a ratio of the silica ($SiO_2$) in said mixture is within 20-35% by weight and a ratio of the alumina ($Al_2O_3$) in said mixture is within 1-10%;
drying said mixture at a temperature above 100° C. for 24 h;
grinding said dried mixture to produce a powder;
shaping and compacting said powder in a wet form to produce a bulk;
melting said bulk at a temperature ranging up to 1650° C. to produce a melt;
quenching said melt; and
grinding said quenched melt to produce a powder, wherein an amount of said calcium-silicate and calcium-aluminate cement present in said prepared powder in the biomaterial is up to 98 weight percent.

15. The method as claimed in claim 7, wherein said radiopaque material is selected from a group comprising of a salt, an oxide of silver, barium, strontium, titanium, bismuth; a metal; heavy metals containing glass frits; a compound containing tungsten; an organo-iodine compound, and a combination thereof and wherein an amount of said radiopaque material is up to 48 weight percent.

16. The method as claimed in claim 7, wherein said nano-particle comprises at least one nano-particle selected from a group consisting of nano-silica, nano-titanium oxide, nano-iron, nano-iron oxide, nano-alumina, nano-zinc oxide, nano-boron, nano-calcium carbonate, nano-clay; nanotubes; nanofibers; nanocomposites, and combinations thereof and wherein an amount of said nano-particle is within 0.5 to 25 percent by weight.

17. The method as claimed in claim 1, wherein said process of inducing a soft and hard tissue in dental tissue comprises:
identifying a tooth cavity to be filled, wherein the tooth cavity comprises of a cavity selected from a group comprising of a cavity with Class I to Class VI standard, a non-standard tooth cavity, a pulp chamber with partial pulpotomy, a pulp chamber with complete pulpotomy, a root canal, a root perforation, an internal root resorption, an external root resorption, and a root-end cavity;
preparing said cavity to be filled in a tooth;
preparing said biomaterial;
applying said biomaterial into said tooth cavity;
creating a first seal for said tooth cavity;
increasing said first seal, wherein said first seal is increased by an expansion of the said applied biomaterial into said tooth cavity, wherein said biomaterial expands three dimensionally wherein said biomaterial expands along a length direction, a width direction and a height direction thereby providing a better adaptation to tooth walls;
releasing a biological active material from said biomaterial for promoting a tissue healing and a tissue generation and a tissue regeneration in said tooth cavity to create an antibacterial environment in said tooth cavity as well as to create a second seal over said first seal via hydroxyapatite formation and wherein said promoting tissue healing/generation/regeneration includes a pulp revitalization, a pulp revascularization, a dentinogenesis, and a cementogenesis, and combinations thereof.

18. The method as claimed in claim 1, wherein a process for inducing or substituting a hard tissue in bone comprises:
identifying a site to be restored in a bone;
preparing said site to be restored in said bone;
preparing said biomaterial;
applying said biomaterial into said insertion site of said bone;
releasing a biological active material from said biomaterial for osteoinduction and/or osteoconduction to promote osteogenesis thereby progressively replacing said biomaterial with a natural bone.

19. The method as claimed in claim 1, further comprises modifying a plurality of components present in the powder component and a mixing ratio of said plurality of components in the powder component and said liquid component to develop a plurality of fast setting or non-fast setting biomaterials in a dental or a medical kit, wherein said dental or medical kit is used for treating an application, wherein said application is selected from a group comprising of vital pulp therapy, direct pulp capping, indirect pulp capping, pulpotomy, pulp revitalization, pulp revascularization, anti external/internal root resorption therapy, root canal sealant, root canal filling, perforation repair, root-end filling, implant biomaterial, bone cement, bone filler, and other related clinical applications.

20. The method as claimed in claim 1, wherein said treated form of said cement mixture is prepared by a process comprising the steps of:

mixing the powder component and the liquid component to form a mixture;

storing the mixture in an incubator at 37° C. and at 95% of humidity for 24 hours to set;

drying the set mixture at more than 100° C. for 24 hour;

grinding the dried set mixture to produce a powder;

storing the powder in a water base solution at 37° C. in an incubator upto 7 days to produce a treated powder with a precipitation of hydroxyapatite;

removing the treated powder containing a precipitate of hydroxyapatite from the incubator;

drying the treated powder containing the precipitate of hydroxyapatite from the water base solution;

dissolving a polymer in a solvent to form a solution, wherein the polymer is selected from a group consisting of a resorbable and biodegradable or nonresorbable naturally-occurring or synthetic polymers or copolymers, and wherein the solvent is chloroform;

adding the dried treated powder containing the precipitate of hydroxyapatite to the solution;

adding camphene to the solution having the dried treated powder containing the precipitate of hydroxyapatite to produce a composite solution;

adding the composite solution into a water bath containing alcohol while stirring to promote a solidification thereby obtaining said treated form of said cement mixture, wherein the said treated from of the said cement mixture is microspheres, wherein said microspheres are obtained by solvent evaporation and sublimation of said camphene.

* * * * *